US012426981B2

(12) United States Patent
Takao et al.

(10) Patent No.: US 12,426,981 B2
(45) Date of Patent: Sep. 30, 2025

(54) GRIP TOOL, GRIP SYSTEM, SLIP DETECTION DEVICE, SLIP DETECTION PROGRAM, AND SLIP DETECTION METHOD

(71) Applicant: National University Corporation Kagawa University, Takamatsu (JP)

(72) Inventors: Hidekuni Takao, Takamatsu (JP); Masao Fujiwara, Takamatsu (JP)

(73) Assignee: National University Corporation Kagawa University, Takamatsu (JP)

( * ) Notice: Subject to any disclaimer, the term of this patent is extended or adjusted under 35 U.S.C. 154(b) by 265 days.

(21) Appl. No.: 17/766,255

(22) PCT Filed: Oct. 2, 2020

(86) PCT No.: PCT/JP2020/037494
§ 371 (c)(1),
(2) Date: Apr. 4, 2022

(87) PCT Pub. No.: WO2021/066122
PCT Pub. Date: Apr. 8, 2021

(65) Prior Publication Data
US 2024/0115343 A1 Apr. 11, 2024

(30) Foreign Application Priority Data
Oct. 4, 2019 (JP) .................. 2019-183388

(51) Int. Cl.
*A61B 90/00* (2016.01)
*A61B 17/29* (2006.01)
(Continued)

(52) U.S. Cl.
CPC .............. *A61B 90/06* (2016.02); *A61B 17/29* (2013.01); *A61B 34/30* (2016.02); *B25J 15/08* (2013.01);
(Continued)

(58) Field of Classification Search
CPC ......... A61B 90/06; A61B 17/29; A61B 34/30; A61B 2090/064; A61B 2562/043;
(Continued)

(56) References Cited

U.S. PATENT DOCUMENTS

| 4,695,963 A | * | 9/1987 | Sagisawa | ................ G01L 5/228 |
| | | | | 414/730 |
| 4,745,812 A | * | 5/1988 | Amazeen | .................. G01L 1/18 |
| | | | | 901/33 |

(Continued)

FOREIGN PATENT DOCUMENTS

| CN | 105947534 A | 9/2016 |
| CN | 107247460 A | 10/2017 |

(Continued)

OTHER PUBLICATIONS

Search Report in corresponding Chinese App. No. 202080068840.5, mailed Feb. 25, 2024, pp. 1-6, CNIPA.

(Continued)

*Primary Examiner* — Andrew P. Restaino
(74) *Attorney, Agent, or Firm* — Modal PLLC

(57) ABSTRACT

Provided is a grip tool that allows detecting a slip of an object. The grip tool includes a pair of grip portions that sandwiches to grip an object; an opening/closing mechanism that opens and closes the pair of grip portions; and at least one sensor unit disposed in one or both of the pair of grip portions. The sensor unit includes a plurality of force sensors disposed in a predetermined distribution. The plurality of force sensors each have a function of measuring forces in triaxial directions received from the object. The sensor unit can measure a load distribution received from the object. The slip of the object is detectable based on the load distribution.

21 Claims, 20 Drawing Sheets

(51) Int. Cl.
*A61B 34/30* (2016.01)
*B25J 15/08* (2006.01)
*G01L 5/162* (2020.01)

(52) U.S. Cl.
CPC ........ *G01L 5/162* (2013.01); *A61B 2090/064* (2016.02); *A61B 2562/043* (2013.01)

(58) Field of Classification Search
CPC . A61B 2017/2926; B25J 15/08; B25J 9/1689; B25J 13/083; G01L 5/162; G01L 5/00; G05B 2219/40155; G05B 2219/45118
See application file for complete search history.

(56) References Cited

U.S. PATENT DOCUMENTS

| | | | |
|---|---|---|---|
| 6,188,331 | B1 | 2/2001 | Zee et al. |
| 2010/0125423 | A1 | 5/2010 | Tsuboi |
| 2011/0106141 | A1 | 5/2011 | Nakamura |
| 2011/0193363 | A1 | 8/2011 | Nishiwaki |
| 2012/0067142 | A1 | 3/2012 | Shimojo |
| 2016/0030240 | A1* | 2/2016 | Gonenc ............. A61B 17/2909 606/205 |
| 2018/0042464 | A1* | 2/2018 | Arai ..................... A61B 1/0014 |
| 2018/0356301 | A1 | 12/2018 | Tomita et al. |
| 2020/0121341 | A1 | 4/2020 | Ogata |

FOREIGN PATENT DOCUMENTS

| | | |
|---|---|---|
| CN | 107696998 A | 2/2018 |
| CN | 108100557 A | 6/2018 |
| CN | 108673551 A | 10/2018 |
| CN | 108946048 A | 12/2018 |
| CN | 109470394 A | 3/2019 |
| JP | S60-000096 U1 | 1/1985 |
| JP | H06-138019 A | 5/1994 |
| JP | H07-186083 A | 7/1995 |
| JP | H08-323678 A | 12/1996 |
| JP | 2004-268160 A | 9/2004 |
| JP | 2005-144573 A | 6/2005 |
| JP | 2005-177977 A | 7/2005 |
| JP | 2006-297542 A | 11/2006 |
| JP | 2008-089522 A | 4/2008 |
| JP | 2009-036557 A | 2/2009 |
| JP | 2009-066683 A | 4/2009 |
| JP | 2010-005732 A | 1/2010 |
| JP | 2010-120111 A | 6/2010 |
| JP | 2010-259677 A | 11/2010 |
| JP | 2010-271242 A | 12/2010 |
| JP | 2011-163945 A | 8/2011 |
| JP | 2013-117458 A | 6/2013 |
| JP | 2015-159840 A | 9/2015 |
| JP | 2017-129586 A | 7/2017 |
| JP | 2018-102634 A | 7/2018 |
| JP | 2019-002905 A | 1/2019 |
| WO | 2010-109932 A1 | 9/2010 |
| WO | 2017217952 A1 | 12/2017 |
| WO | 2018-061705 A1 | 4/2018 |

OTHER PUBLICATIONS

Search Report in corresponding Chinese App. No. 202080068840.5, Aug. 27, 2024, 5 pages, CNIPA.

Taiyu Okatani et al., "A MEMS Slip Sensor: Estimations of Triaxial Force and Coefficient of Static Friction for Prediction of a Slip," Dig. of Technical Papers of 19th Int'l Conf. on Solid-State Sensors, Actuators and Microsystems (Transducers 2017), Jun. 18-22, 2017, pp. 75-77, 2017, Kaohsiung, Taiwan.

International Search Report in International Application PCT/JP2020/037494, dated Dec. 15, 2020, pp. 1-3.

Extended European Search Report in corresponding 20872060.7, Aug. 26, 2022, 9 pages, EPO, Munich, Germany.

Uikyum Kim et al., "Design and Realization of Grasper-Integrated Force Sensor for Minimally Invasive Robotic Surgery," 2014 IEEE/RSJ Int'l Conf. on Intelligent Robots and Sys., Sep. 14-18, 2014, 4321-4326, IEEE, Chicago, IL, USA.

\* cited by examiner

FIG. 3
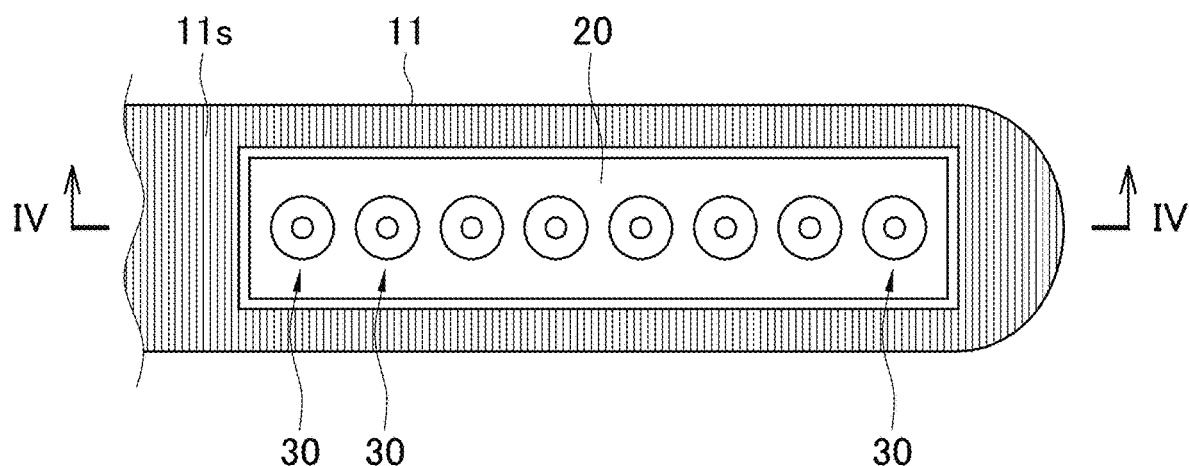
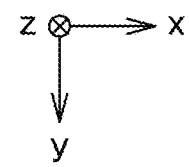

FIG. 6A
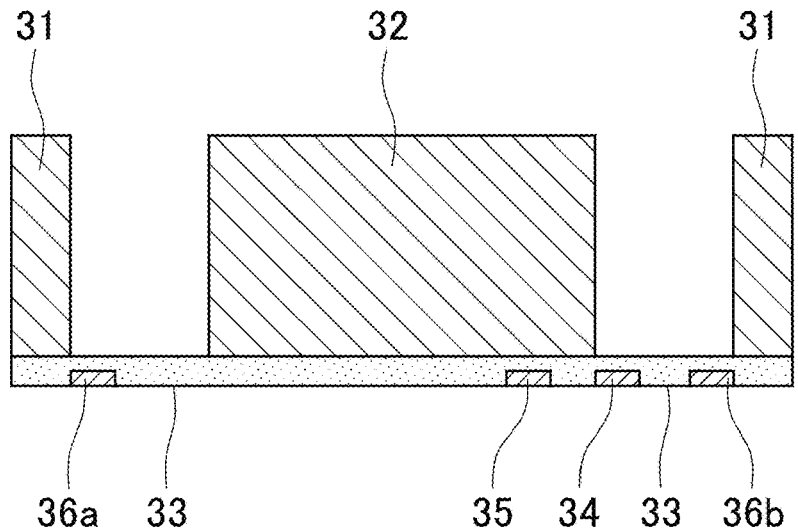
FIG. 6B
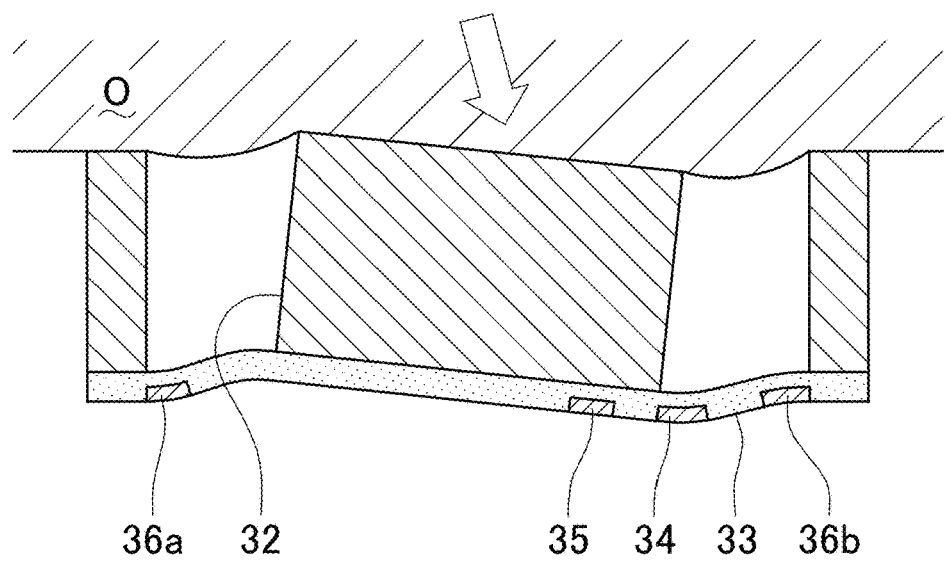
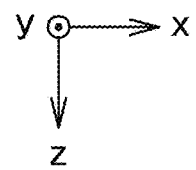

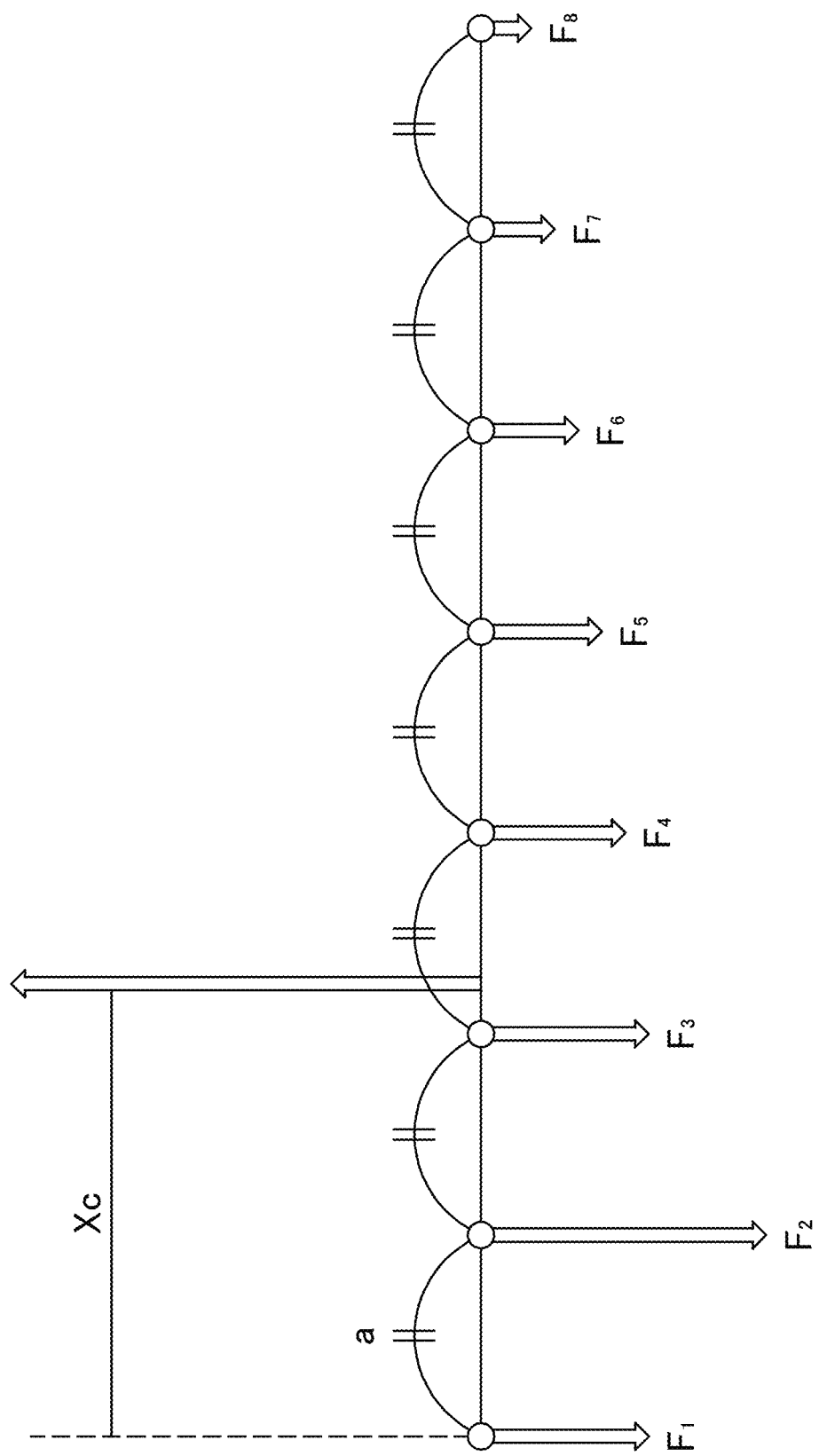

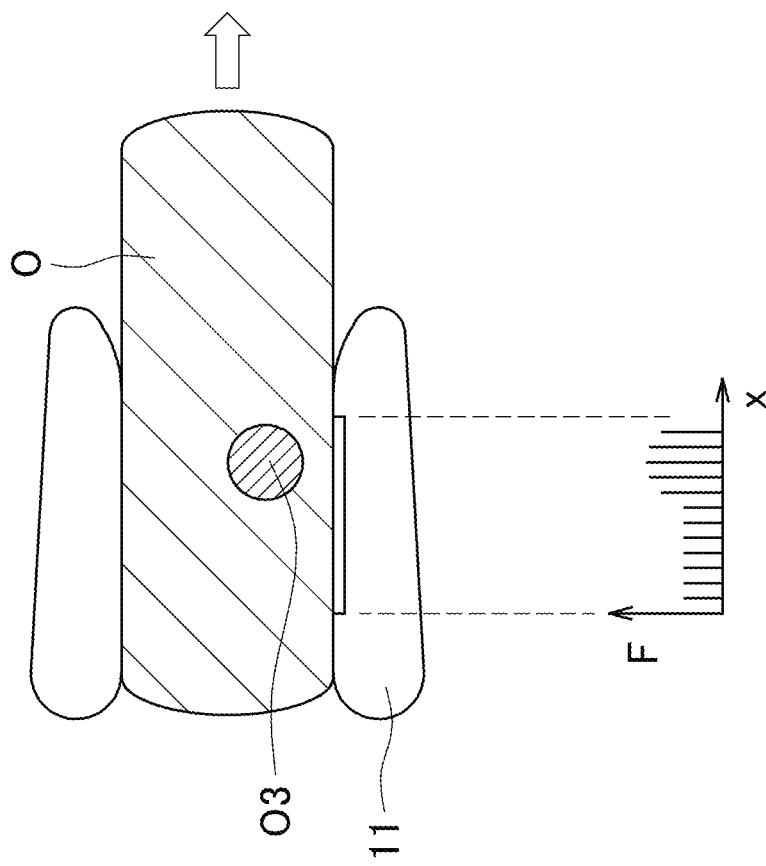
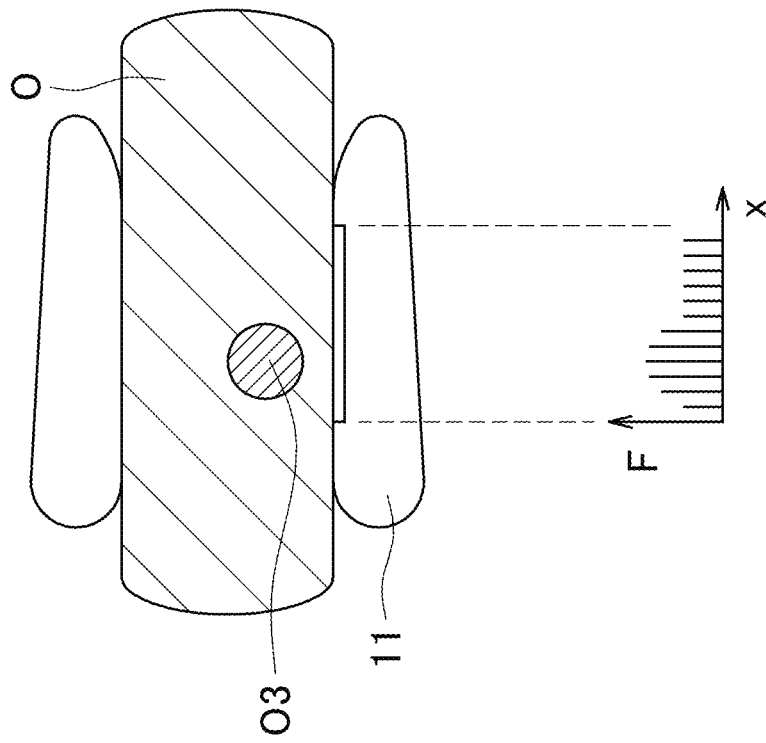

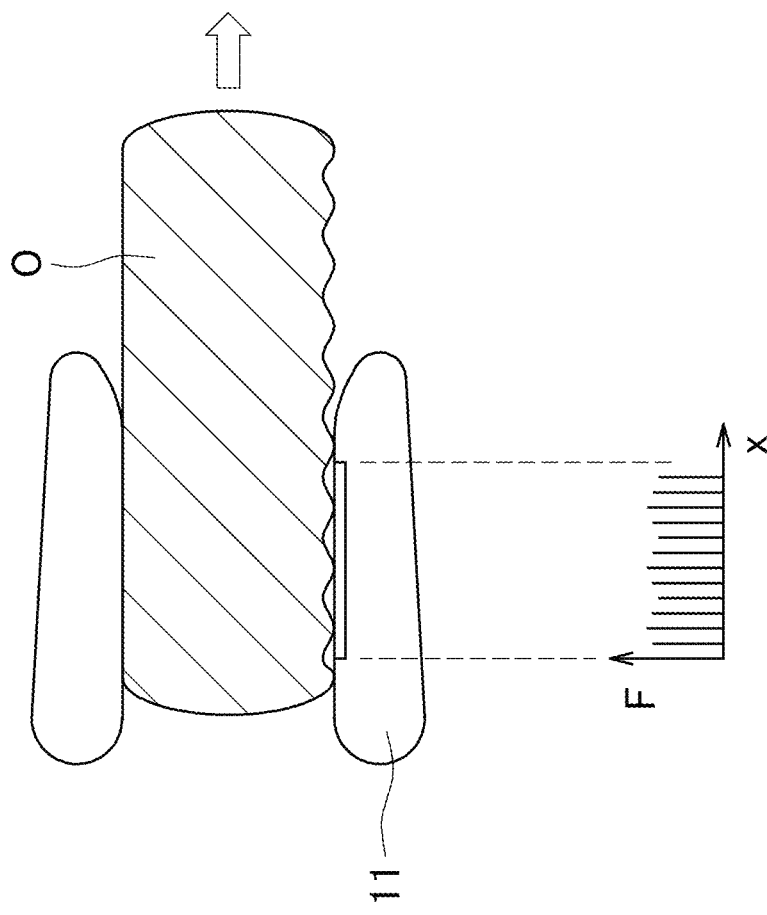
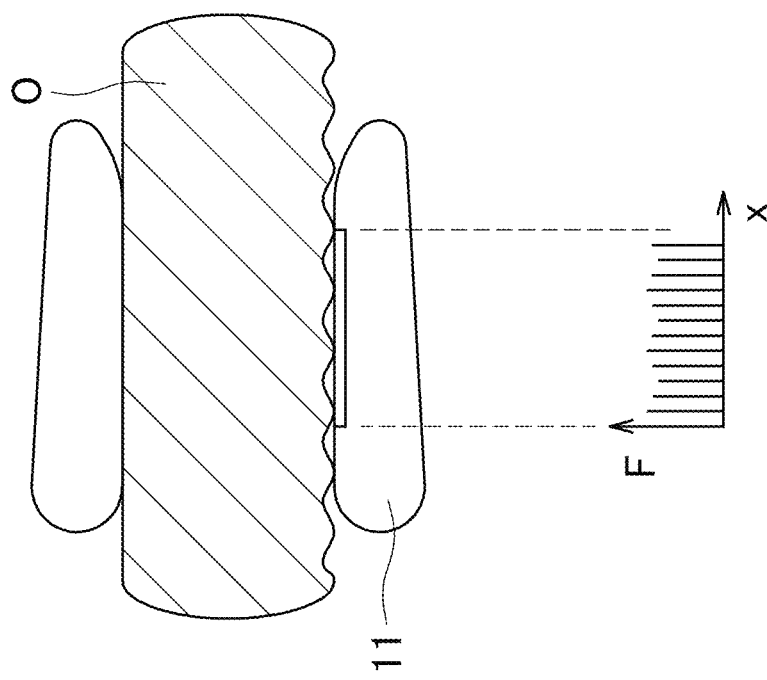

FIG. 13
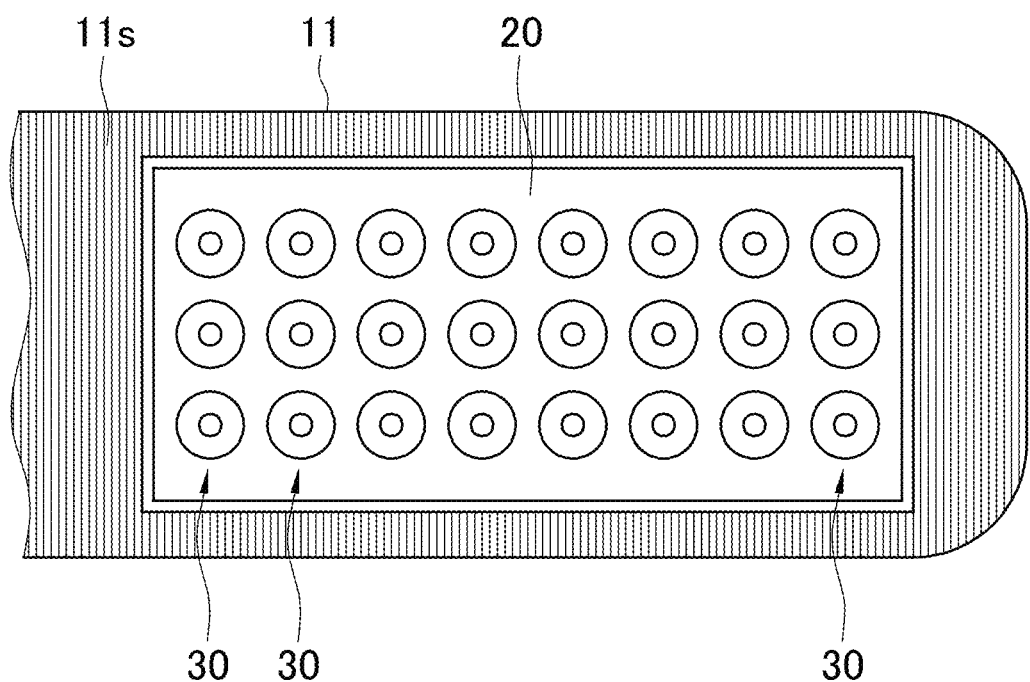
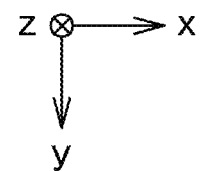

FIG. 15A
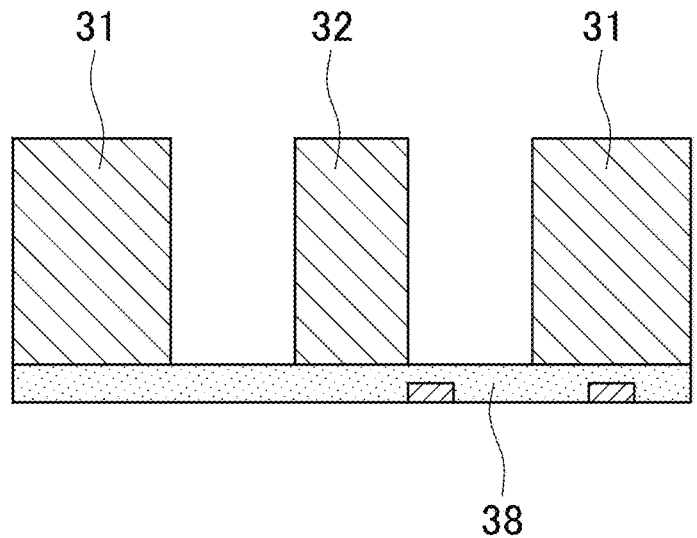
FIG. 15B
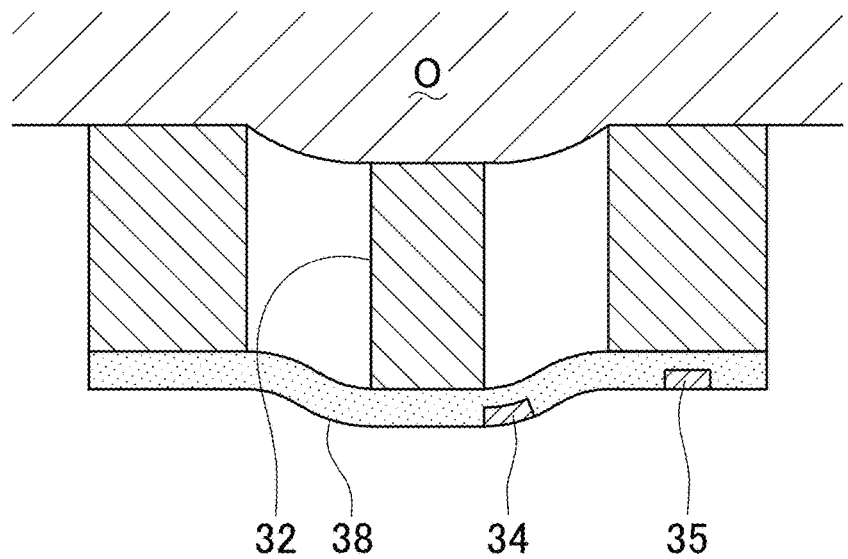
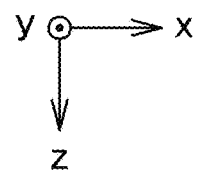

FIG. 17
Front Surface
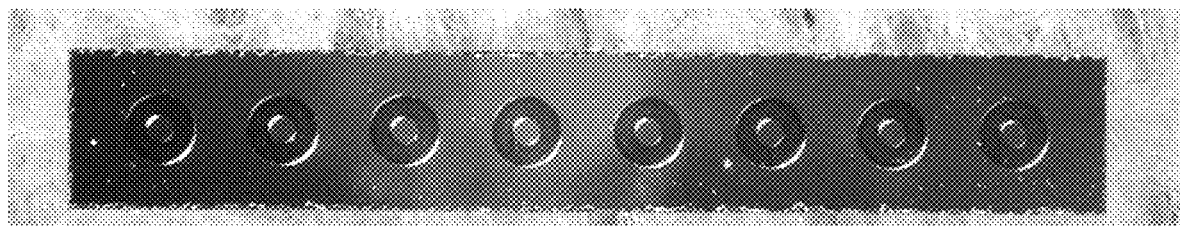
Bach Surface
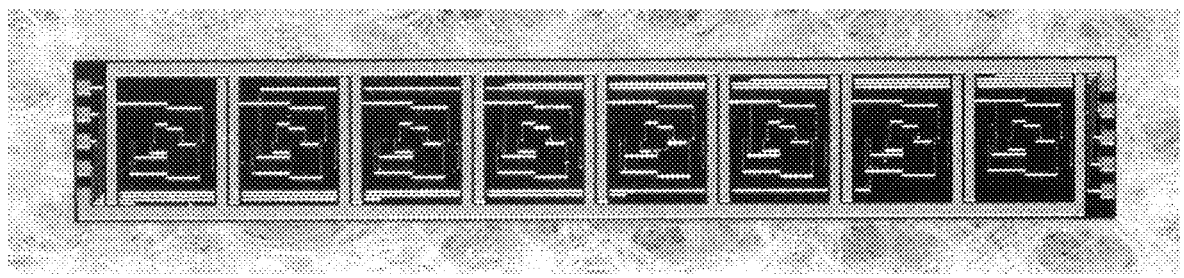

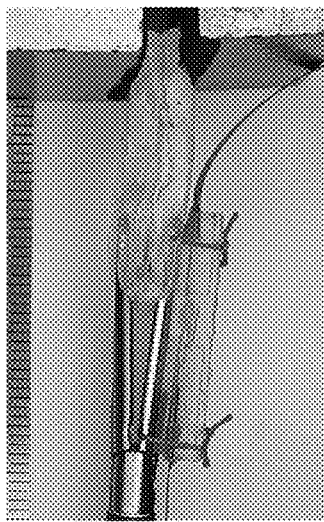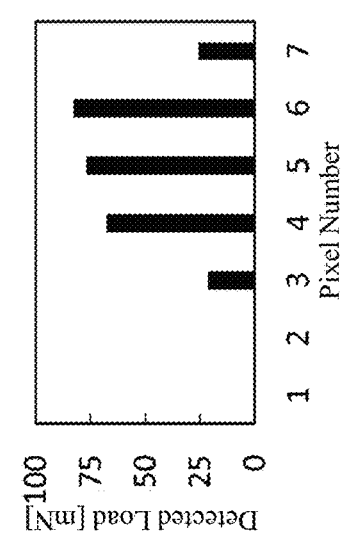
FIG. 18A  FIG. 18B  FIG. 18C
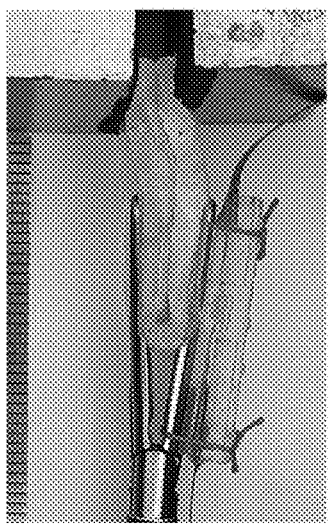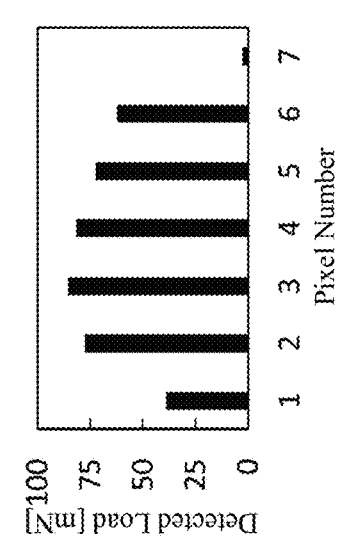
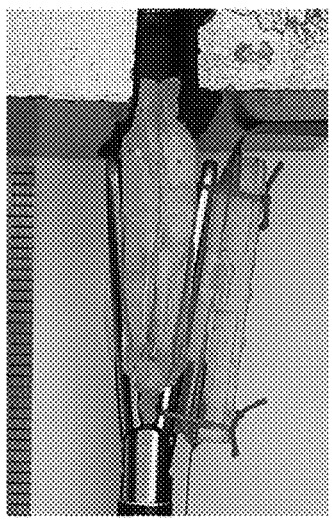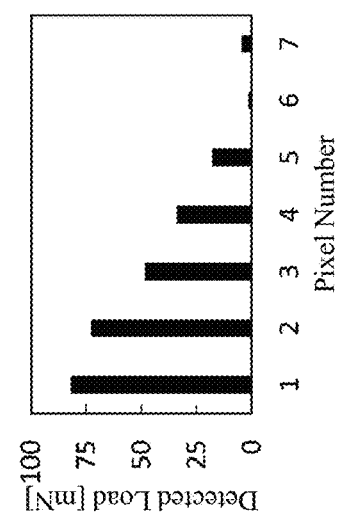

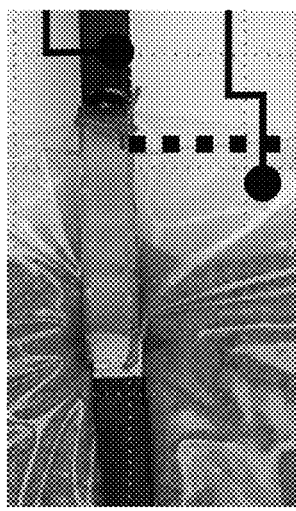 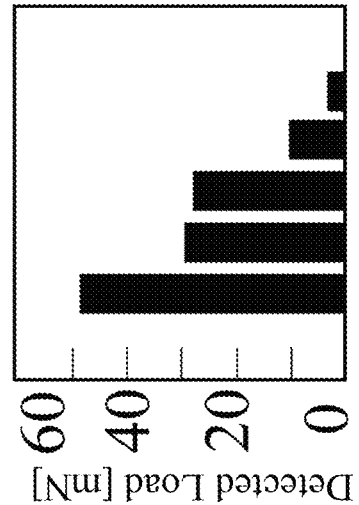
FIG. 19A — After 4.5 Seconds
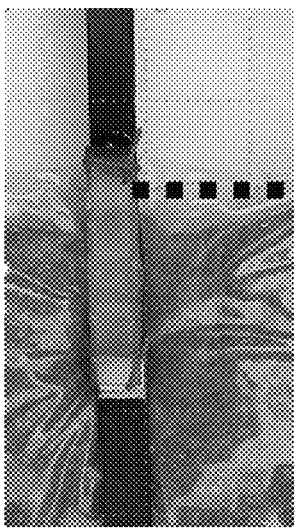 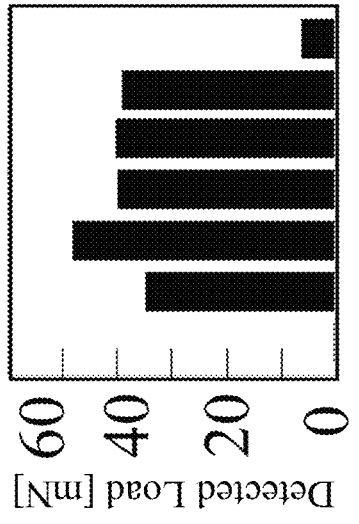
FIG. 19B — After 8.2 Seconds
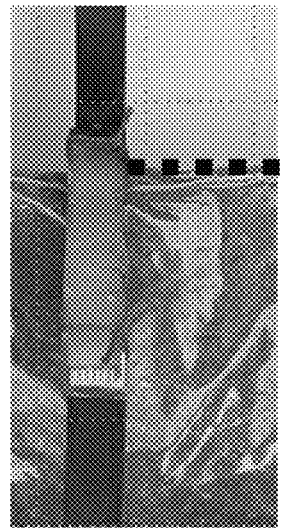 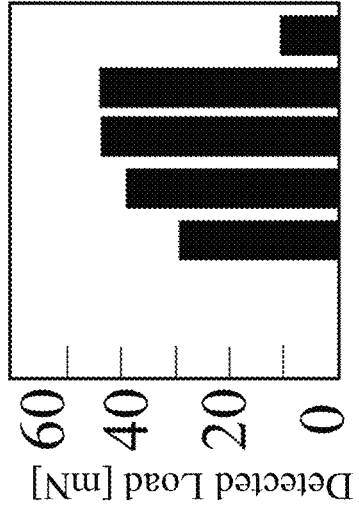
FIG. 19C — After 16.1 Seconds

GRIP TOOL, GRIP SYSTEM, SLIP DETECTION DEVICE, SLIP DETECTION PROGRAM, AND SLIP DETECTION METHOD

CROSS-REFERENCES TO RELATED APPLICATIONS

This application is the U.S. National Phase of PCT International Application No. PCT/JP2020/037494, filed on Oct. 2, 2020. That application claims priority to Japanese Patent Application No. 2019-183388, filed Oct. 4, 2019. The contents of the U.S. National Phase of PCT International Application No. PCT/JP2020/037494, filed on Oct. 2, 2020 is herein incorporated by reference in its entirety.

TECHNICAL FIELD

The present invention relates to a grip tool, a grip system, a slip detection device, a slip detection program, and a slip detection method. More specifically, the present invention relates to a grip tool, such as a forceps for medical treatment, a robot hand, or a gripper, a grip system including the grip tool, a device, a program, and a method for detecting a slip of an object gripped by the grip tool.

BACKGROUND ART

There is known an endoscopic surgery as one kind of minimally invasive surgery. The endoscopic surgery is performed under a difficult condition where only limited visual information displayed on a monitor is available. Thus, it has been attempted to attach sensors to endoscopes and provide information in a body to doctors. For example, WO 2018/061705 discloses a technique of measuring a gas pressure in a body by a pressure sensor attached to a distal end of an endoscope.

Since a human organ treated in the endoscopic surgery is slippery, skill of a surgeon is required to grip the organ with forceps so as not to slip it down. Not only the forceps but also other grip tools, such as a robot hand and a gripper, are often used in a situation where a slippery object is gripped.

For a slip that occurs when a robot hand grips an object, A MEMS slip sensor: Estimations of triaxial force and coefficient of static friction for prediction of a slip, Taiyu Okatani; Akihito Nakai; Tomoyuki Takahata; Isao Shimoyama, Digest of Technical Papers of 19th International Conference on Solid-State Sensors, Actuators and Microsystems (TRANSDUCERS2017), DOI: 10.1109/TRANSDUCERS.2017.7993991, pp. 75-77, 2017, discloses a technique for prediction of occurrence of a slip by forces in triaxial directions and a static friction coefficient measured by a triaxial force sensor stacked and mounted on a grip portion.

BRIEF SUMMARY

However, the technique of Okatani et al. cannot detect a slip itself of an object. Many human organs are in a low friction state where the organs are covered with a lubricant film such as body fluid. Furthermore, the human digestive organ wall is generally divided into four layers, and, specifically, a slip easily occurs between a mucosal layer and a muscle layer. It is difficult to determine the slip of the slippery object like the organ based on a frictional force.

Therefore, in consideration of the above-described circumstances, the present invention has an object to provide a grip tool that allows detecting a slip of an object, a grip system including the grip tool, a device, a program and a method that detects the slip of the object gripped with the grip tool.

(Grip System)

A grip system according to a first aspect includes a grip tool; and a slip detection device. The grip tool includes a pair of grip portions that sandwiches to grip an object; an opening/closing mechanism that opens and closes the pair of grip portions; and at least one sensor unit disposed in one or both of the pair of grip portions. The sensor unit includes a plurality of force sensors disposed in a predetermined distribution. The plurality of force sensors each have a function of measuring forces in triaxial directions received from the object. The slip detection device detects a slip of the object based on a load distribution measured by the sensor unit. The load distribution is a distribution of a combined load obtained by combining the forces in the triaxial directions.

In the grip system according to a second aspect, which is in the first aspect, the slip detection device obtains a center position of the load distribution and detects the slip of the object based on a temporal change of the center position.

In the grip system according to a third aspect, which is in the first aspect, the slip detection device obtains a peak position of the load distribution and detects the slip of the object based on a temporal change of the peak position.

In the grip system according to a fourth aspect, which is in the first aspect, the slip detection device detects the slip of the object based on a parallel movement of the load distribution.

A grip system according to a fifth aspect includes a grip tool; and a slip detection device. The grip tool includes a pair of grip portions that sandwiches to grip an object; an opening/closing mechanism that opens and closes the pair of grip portions; and at least one sensor unit disposed in one or both of the pair of grip portions. The sensor unit includes a plurality of force sensors disposed in a predetermined distribution. The plurality of force sensors each have a function of measuring forces in triaxial directions received from the object. The slip detection device obtains a static friction coefficient of the object from a perpendicular load measurement value and a frictional force measurement value measured by the sensor unit immediately before the object starts to slip.

In the grip system according to a sixth aspect, which is in the fifth aspect, the slip detection device preliminarily obtains and stores the static friction coefficient, obtains a maximum static frictional force from the static friction coefficient and a current perpendicular load measurement value, and predicts a start of slipping of the object based on a relation between the current frictional force measurement value and the maximum static frictional force.

(Slip Detection Device)

A slip detection device according to a seventh aspect detects a slip of an object gripped by a grip tool including a grip portion having a sensor unit with a plurality of force sensors. The slip detection device detects a slip of the object based on a load distribution measured by the sensor unit. The load distribution is a distribution of a combined load obtained by combining forces in triaxial directions that the force sensors receive from the object.

In the slip detection device according to an eighth aspect, which is in the seventh aspect, the slip detection device obtains a center position of the load distribution and detects the slip of the object based on a temporal change of the center position.

In the slip detection device according to a ninth aspect, which is in the seventh aspect, the slip detection device obtains a peak position of the load distribution and detects the slip of the object based on a temporal change of the peak position.

In the slip detection device according to a tenth aspect, which is in the seventh aspect, the slip detection device detects the slip of the object based on a parallel movement of the load distribution.

A slip detection device according to an eleventh aspect predicts a slip of an object gripped by a grip tool including a grip portion having a sensor unit with a plurality of force sensors. The slip detection device obtains a static friction coefficient of the object from a perpendicular load measurement value and a frictional force measurement value measured by the sensor unit immediately before the object starts to slip.

In the slip detection device according to a twelfth aspect, which is in the eleventh aspect, the slip detection device preliminarily obtains and stores the static friction coefficient, obtains a maximum static frictional force from the static friction coefficient and a current perpendicular load measurement value, and predicts a start of slipping of the object based on a relation between the current frictional force measurement value and the maximum static frictional force.

(Slip Detection Program)

A slip detection program according to a thirteenth aspect causes a computer to execute a process for detecting a slip of an object gripped by a grip tool including a grip portion having a sensor unit with a plurality of force sensors. The process includes detecting a slip of the object based on a load distribution measured by the sensor unit. The load distribution is a distribution of a combined load obtained by combining forces in triaxial directions that the force sensors receive from the object.

In the slip detection program according to a fourteenth aspect, which is in the thirteenth aspect, the process includes obtaining a center position of the load distribution; and detecting the slip of the object based on a temporal change of the center position.

In the slip detection program according to a fifteenth aspect, which is in the thirteenth aspect, the process includes obtaining a peak position of the load distribution; and detecting the slip of the object based on a temporal change of the peak position.

In the slip detection program according to a sixteenth aspect, which is in the thirteenth aspect, the process includes detecting the slip of the object based on a parallel movement of the load distribution.

A slip detection program according to a seventeenth aspect causes a computer to execute a process for predicting a slip of an object gripped by a grip tool including a grip portion having a sensor unit with a plurality of force sensors. The process includes obtaining a static friction coefficient of the object from a perpendicular load measurement value and a frictional force measurement value measured by the sensor unit immediately before the object starts to slip.

In the slip detection program according to an eighteenth aspect, which is in the seventeenth aspect, the process includes preliminarily obtaining and storing the static friction coefficient; obtaining a maximum static frictional force from the static friction coefficient and a current perpendicular load measurement value; and predicting a start of slipping of the object based on a relation between the current frictional force measurement value and the maximum static frictional force.

(Slip Detection Method)

A slip detection method according to a nineteenth aspect detects a slip of an object gripped by a grip tool including a grip portion having a sensor unit with a plurality of force sensors. The slip detection method includes detecting a slip of the object based on a load distribution measured by the sensor unit. The load distribution is a distribution of a combined load obtained by combining forces in triaxial directions that the force sensors receive from the object.

In the slip detection method according to a twentieth aspect, which is in the nineteenth aspect, the detecting includes obtaining a center position of the load distribution; and detecting the slip of the object based on a temporal change of the center position.

In the slip detection method according to a twenty-first aspect, which is in the nineteenth aspect, the detecting includes obtaining a peak position of the load distribution; and detecting the slip of the object based on a temporal change of the peak position.

In the slip detection method according to a twenty-second aspect, which is in the nineteenth aspect, the detecting includes detecting the slip of the object based on a parallel movement of the load distribution.

A slip detection method according to a twenty-third aspect predicts a slip of an object gripped by a grip tool including a grip portion having a sensor unit with a plurality of force sensors. The slip detection method includes obtaining a static friction coefficient of the object from a perpendicular load measurement value and a frictional force measurement value measured by the sensor unit immediately before the object starts to slip.

In the slip detection method according to a twenty-fourth aspect, which is in the twenty-third aspect, includes preliminarily obtaining the static friction coefficient; obtaining a maximum static frictional force from the static friction coefficient and a current perpendicular load measurement value; and predicting a start of slipping of the object based on a relation between the current frictional force measurement value and the maximum static frictional force.

(Grip System)

According to the first to fourth aspects, since the slip of the object is detected based on the load distribution, the slip can be detected even in a slippery object that is less likely to generate friction.

According to the fifth aspect, by obtaining the friction coefficient of the object, the slipperiness of the object can be evaluated.

According to the sixth aspect, by reflecting the prediction of the start of slipping of the object to the operation of the grip tool, the object can be maintained without slipping the object.

(Slip Detection Device)

According to the seventh to tenth aspects, since the slip of the object is detected based on the load distribution, the slip can be detected even in a slippery object that is less likely to generate friction.

According to the eleventh aspect, by obtaining the friction coefficient of the object, the slipperiness of the object can be evaluated.

According to the twelfth aspect, by reflecting the prediction of the start of slipping of the object to the operation of the grip tool, the object can be maintained without slipping the object.

(Slip Detection Program)

According to the thirteenth to sixteenth aspects, since the slip of the object is detected based on the load distribution, the slip can be detected even in a slippery object that is less likely to generate friction.

According to the seventeenth aspect, by obtaining the friction coefficient of the object, the slipperiness of the object can be evaluated.

According to the eighteenth aspect, by reflecting the prediction of the start of slipping of the object to the operation of the grip tool, the object can be maintained without slipping the object.

(Slip Detection Method)

According to the nineteenth to twenty-second aspects, since the slip of the object is detected based on the load distribution, the slip can be detected even in a slippery object that is less likely to generate friction.

According to the twenty-third aspect, by obtaining the friction coefficient of the object, the slipperiness of the object can be evaluated.

According to the twenty-fourth aspect, by reflecting the prediction of the start of slipping of the object to the operation of the grip tool, the object can be maintained without slipping the object.

BRIEF DESCRIPTION OF DRAWINGS

FIG. 3 is a plan view of a grip portion of the first embodiment.

FIG. 6A is a cross-sectional view taken along the line VIa-VIa in FIG. 5.

FIG. 6B is a longitudinal cross-sectional view of the force sensor in a state where an external force is acting.

FIG. 9 is an explanatory view of how to obtain a center position of the load distribution.

FIG. 11A is a side view and a load distribution in a state where a grip portion grips an object.

FIG. 11B is a side view and a load distribution in a state where the object is slipped.

FIG. 12A is a side view and a load distribution in a state where the grip portion grips an object.

FIG. 12B is a side view and a load distribution in a state where the object is slipped.

FIG. 13 is a plan view of a grip portion of a third embodiment.

FIG. 15A is a cross-sectional view taken along the line XVa-XVa in FIG. 14.

FIG. 15B is a longitudinal cross-sectional view of the force sensor in a state where an external force is acting.

FIG. 17 is a photograph of a sensor unit.

FIG. 18A is a photograph and a load distribution in a state where a gel body is gripped with an entire grip portion of forceps.

FIG. 18B is a photograph and a load distribution in a state where the gel body is moved by 5 mm.

FIG. 18C is a photograph and a load distribution in a state where the gel body is moved by 10 mm.

FIG. 19A is a photograph and a load distribution of a state 4.5 seconds after gripping a two-layer body.

FIG. 19B is a photograph and a load distribution of a state 8.2 seconds after gripping the two-layer body.

FIG. 19C is a photograph and a load distribution of a state 16.1 seconds after gripping the two-layer body.

DETAILED DESCRIPTION OF EMBODIMENTS

Next, embodiments of the present invention will be described based on the drawings.

First Embodiment (Grip System)

Figure 1:
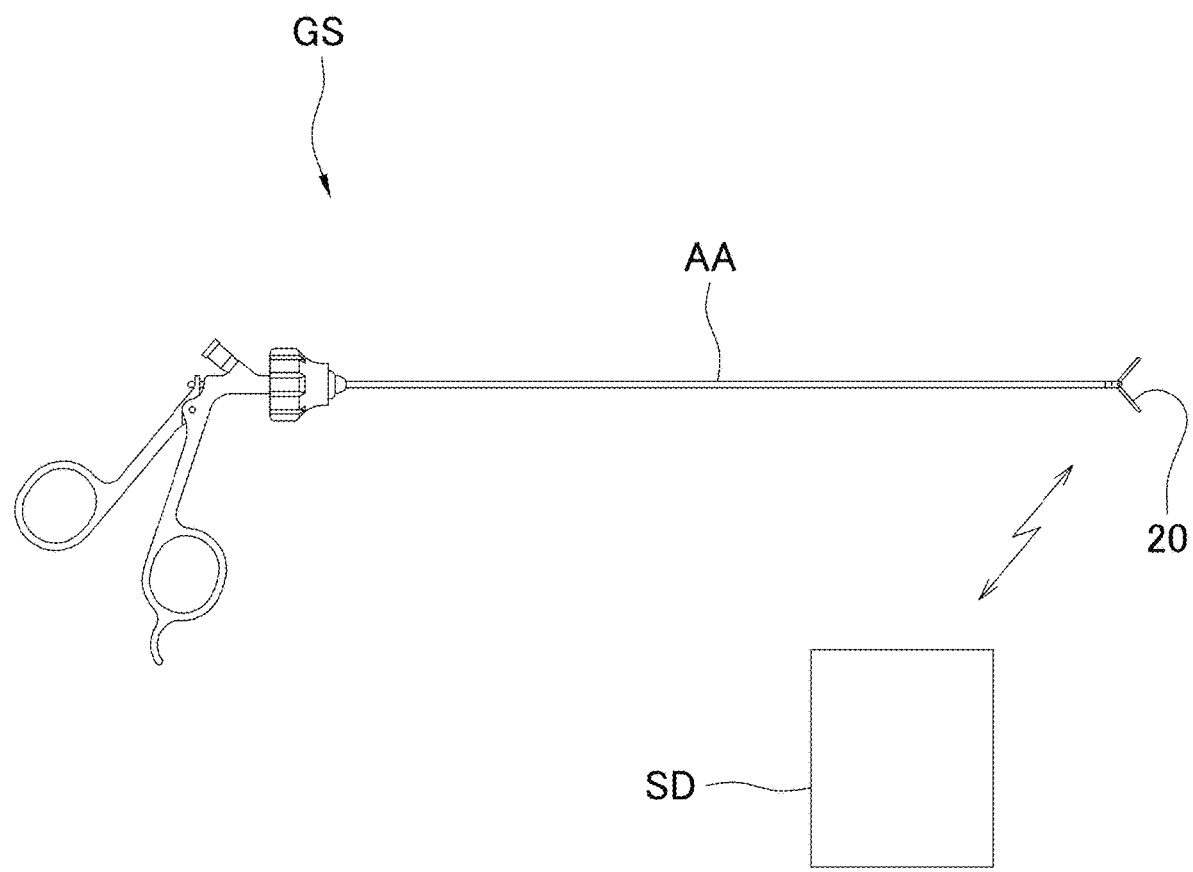
FIG. 1 is an explanatory view of a grip system according to a first embodiment.

As illustrated in FIG. 1, a grip system GS according to the first embodiment of the present invention includes a grip tool AA and a slip detection device SD.

The grip tool AA is a tool to grip an object. As the grip tool AA, for example, a forceps for medical treatment, a robot hand, a gripper, and the like are included. The forceps include the one used alone, the one used in combination with an endoscope, and the one incorporated into a surgical robot. The grip tool AA may be incorporated into a manipulator of a robot for, for example, industrial use and household use. Furthermore, the grip tool AA may be a gripper used as, for example, a tool. In FIG. 1, an example of the forceps is illustrated as the grip tool AA.

As described below, the grip tool AA includes a sensor unit 20. The slip detection device SD detects a slip of an object gripped with the grip tool AA, based on data obtained by the sensor unit 20. The slip detection device SD is a computer constituted of a CPU, a memory and the like. Installing a slip detection program into the computer achieves a function as the slip detection device SD. The slip detection program may be stored into a computer readable storage medium (including a non-transitory storage medium). The sensor unit 20 is coupled to the slip detection device SD by wired or wireless communication. The data obtained by the sensor unit 20 is input into the slip detection device SD.

(Grip Tool)

Figure 2:
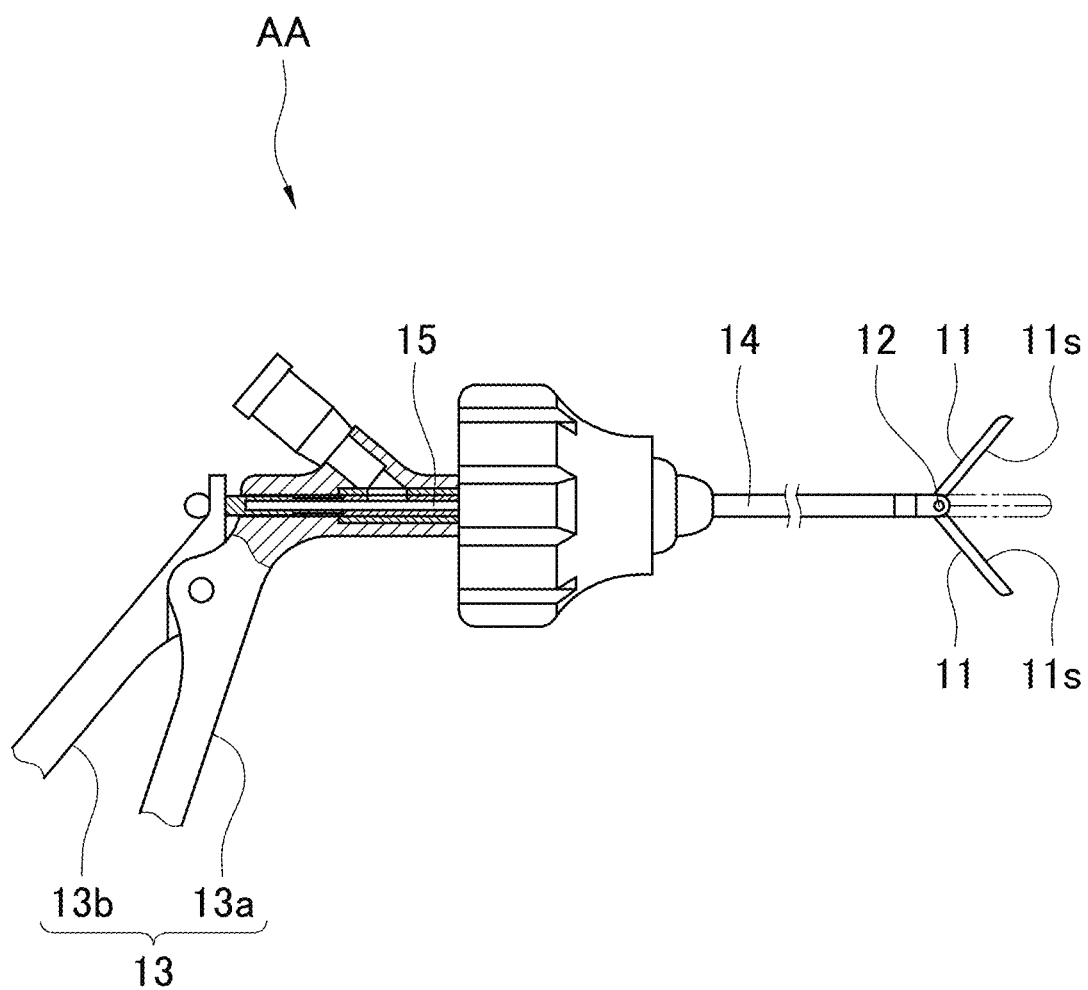
FIG. 2 is a side view of a grip tool of the first embodiment.

As illustrated in FIG. 2, the grip tool AA includes a pair of grip portions 11, 11. Each grip portion 11 is a rod-shaped member. A base end of one grip portion 11 is coupled to a base end of another grip portion 11 by a pin 12. Rotation of both the grip portions 11, 11 around the pin 12 opens and closes the grip portions 11, 11. The solid lines in FIG. 2 indicate a state where the grip portions 11, 11 are opened, and the dash-dotted lines indicate a state where the grip portions 11, 11 are closed. The grip tool AA of the embodiment has the pair of grip portions 11, 11 that open and close like scissors.

Closing the pair of grip portions 11, 11 allows the pair of grip portions 11, 11 to sandwich to grip an object. Opening the pair of grip portions 11, 11 allows the pair of grip portions 11, 11 to release the gripped object. A surface of each grip portion 11 that is opposed to another grip portion 11 is referred to as a grip surface 11s. When an object is gripped by the grip portions 11, 11, the grip surfaces 11s come in contact with the object. In order to increase friction with the object, the grip surfaces 11s may be disposed with unevenness. The grip surfaces 11s may be a flat surface or may be a curved surface.

The grip tool AA has an opening/closing mechanism that opens and closes the pair of grip portions 11, 11. The opening/closing mechanism of the embodiment is mainly constituted of a handle 13, a shaft 14, and a rod 15. The handle 13 is a scissors type handle where a fixed handle 13a is coupled to a movable handle 13b with a pin. A base end of the hollow shaft 14 is secured to the fixed handle 13a. The pair of grip portions 11, 11 are coupled to a distal end of the shaft 14 by the pin 12. The rod 15 is inserted inside the shaft 14. A base end of the rod 15 is secured to the movable handle 13b. A distal end of the rod 15 is coupled to the pair of grip portions 11, 11.

When a surgeon grips the handle 13 and opens and closes it, the opening/closing operation is conveyed via the rod 15, and the pair of grip portions 11, 11 open and close. This allows the surgeon to perform an opening/closing operation of the grip portions 11, 11.

As in the embodiment, both the pair of grip portions 11, 11 may be constituted to rotate with respect to the shaft 14. One grip portion 11 may be constituted to be fixed with respect to the shaft 14, and another grip portion 11 may be constituted to rotate with respect to the shaft 14.

(Sensor Unit)

Figure 4:
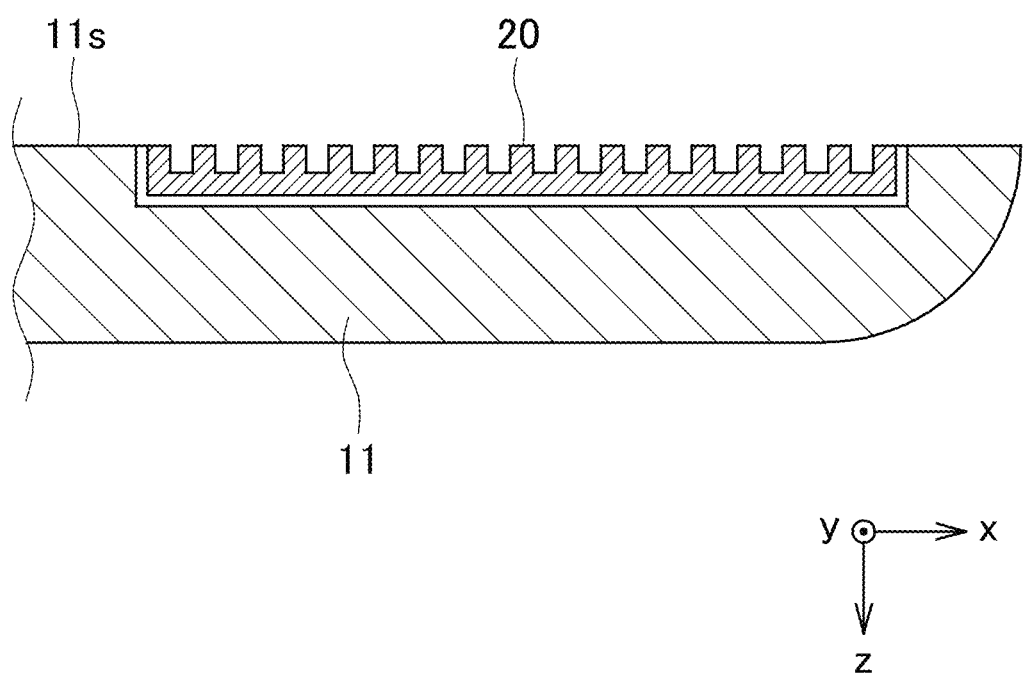
FIG. 4 is a cross-sectional view taken along the line IV-IV in FIG. 3.

As illustrated in FIG. 3 and FIG. 4, the grip portion 11 is provided with the sensor unit 20. When an object is gripped by the grip portions 11, 11 the sensor unit 20 comes in contact with the object. One sensor unit 20 may be disposed in one of the pair of grip portions 11, 11. One sensor unit 20 may be disposed in each of the pair of grip portions 11, 11.

As illustrated in FIG. 3 and FIG. 4, an x-axis, a y-axis, and a z-axis are defined. The x-axis extends along a direction from a base end of the grip portion 11 toward a distal end of the grip portion 11. The y-axis is perpendicular with respect to the x-axis and extends along a width direction of the grip portion 11. The z-axis is perpendicular with respect to the x-axis and the y-axis and extends along a direction perpendicular with respect to the grip surface 11s.

The sensor unit 20 is a rectangular plate-shaped member in plan view. One principal surface of the sensor unit 20 is referred to as a sensing surface. The sensor unit 20 is secured inside the grip portion 11 such that the sensing surface is constituted to be flush with the grip surface 11s. The sensing surface of the sensor unit 20 may be a flat surface. When the grip surface 11s is a curved surface, the sensing surface may be constituted to be a curved surface along the grip surface 11s.

The sensor unit 20 has a plurality of force sensors 30 disposed in a predetermined distribution. The sensor unit 20 of the embodiment has eight force sensors 30 linearly disposed side by side in a row along the x-axis. While the force sensors 30 are preferably disposed at equal intervals, they may be disposed at uneven intervals. The number of the force sensors 30 is not limited to eight. It is only necessary that the sensor unit 20 has equal to or more than two force sensors 30.

(Force Sensor)

Each force sensor 30 has a function of measuring a force received from an object. The force sensor 30 of the embodiment has a function of measuring forces in triaxial directions. Here, the forces in the triaxial directions are constituted of a normal force acting in a direction (the z-axis direction) perpendicular to the sensing surface and tangential forces acting in two directions (the x-axis direction and the y-axis direction) parallel to the sensing surface. The constitution of the force sensor 30 is not specifically limited, for example, it is only necessary that it has a constitution described below.

Figure 5:
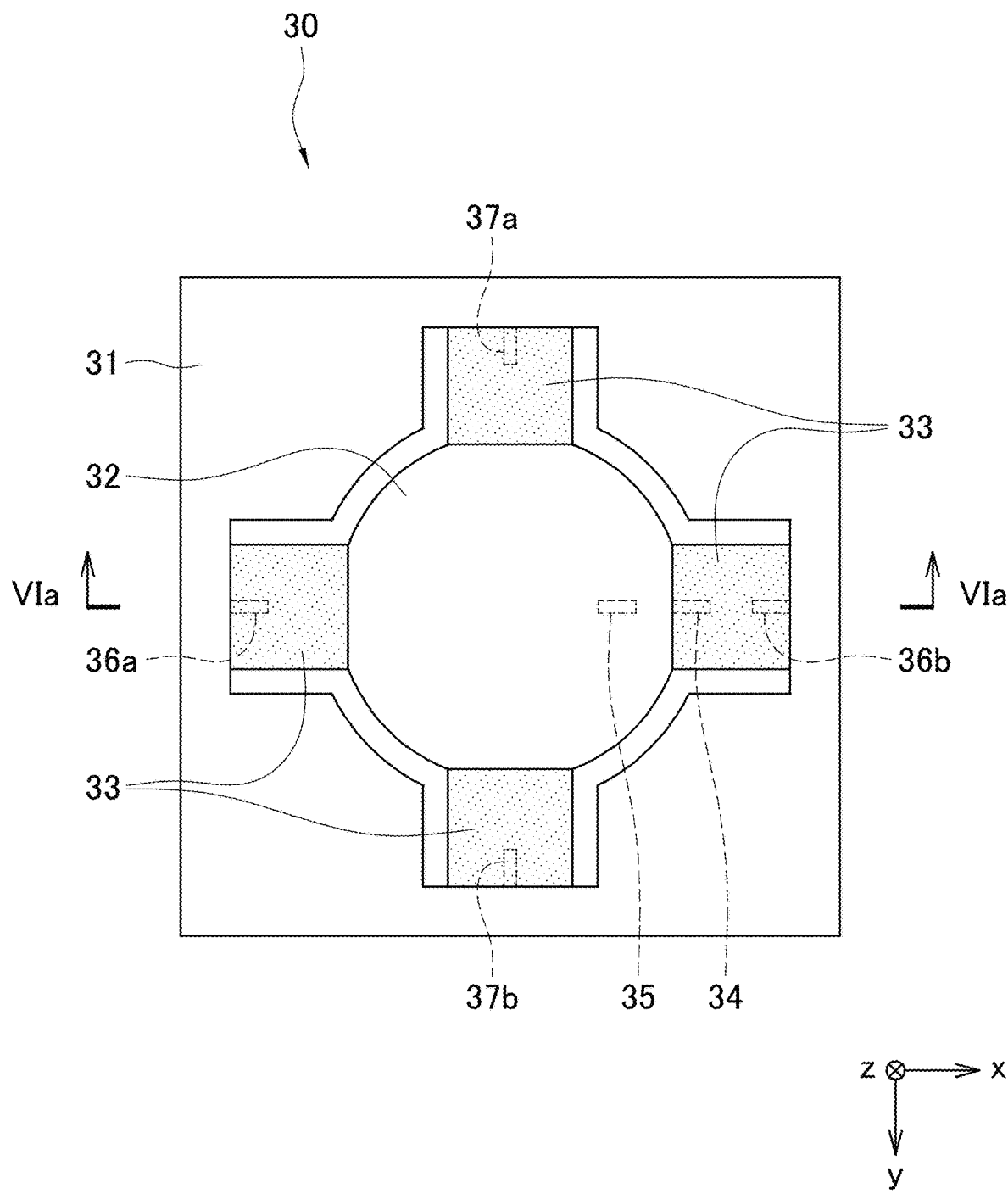
FIG. 5 is a plan view of a force sensor of the first embodiment.

As illustrated in FIG. 5 and FIG. 6A, the force sensor 30 includes a frame 31 and a contact element 32. The contact element 32 is disposed in a space portion formed in the frame 31. The contact element 32 is supported in the frame 31 by four beams 33 disposed in a cross shape. A clearance where the contact element 32 is swingable is disposed between the frame 31 and the contact element 32.

An upper surface of the frame 31 and an upper end surface of the contact element 32 constitute the sensing surface. It is only necessary that the upper end surface of the contact element 32 has a height identical to the upper surface of the frame 31. The upper end surface of the contact element 32 may be protruded upward with respect to the upper surface of the frame 31 or may be buried downward with respect to the upper surface of the frame 31.

A size of the force sensor 30 is not specifically limited, for example, it is 0.5 mm to 5 mm square in plan view. A thickness of the force sensor 30 is, for example, 100 μm to 1 mm. A thickness of the beam 33 is, for example, 10 μm to 30 μm.

As illustrated in FIG. 6B, when an object O comes into contact with the sensing surface of the force sensor 30, the contact element 32 sinks downward (the z-axis direction) by a force received from the object O. As a result, the beam 33 bends. When a direction of the force received from the object O is inclined with respect to the z-axis direction, the contact element 32 is inclined with respect to the z-axis direction.

Due to a perpendicular displacement and the inclination of the contact element 32, a strain is generated in the beam 33. In order to detect the strain of the beam 33, five strain detection elements 34, 36a, 36b, 37a, 37b are disposed in the beam 33. The strain detection elements 34, 36a, 36b, 37a, 37b are, for example, piezo resistance elements.

The strain detection element 34 is used for detecting the perpendicular displacement of the contact element 32. Hereinafter, the strain detection element 34 is referred to as a z-axis strain detection element 34. A reference resistor 35 used in combination with the z-axis strain detection element 34 is disposed in the force sensor 30. The reference resistor 35 is disposed at a position that is not affected by the bend of the beam 33, for example, on a lower surface of the contact element 32.

The strain detection elements 36a, 36b are disposed at a position sandwiching the contact element 32 along the x-axis. Hereinafter, the strain detection elements 36a, 36b are referred to as x-axis strain detection elements 36a, 36b. The strain detection elements 37a, 37b are disposed at a position sandwiching the contact element 32 along the y-axis. Hereinafter, the strain detection elements 37a, 37b are referred to as y-axis strain detection elements 37a, 37b.

Figure 7:
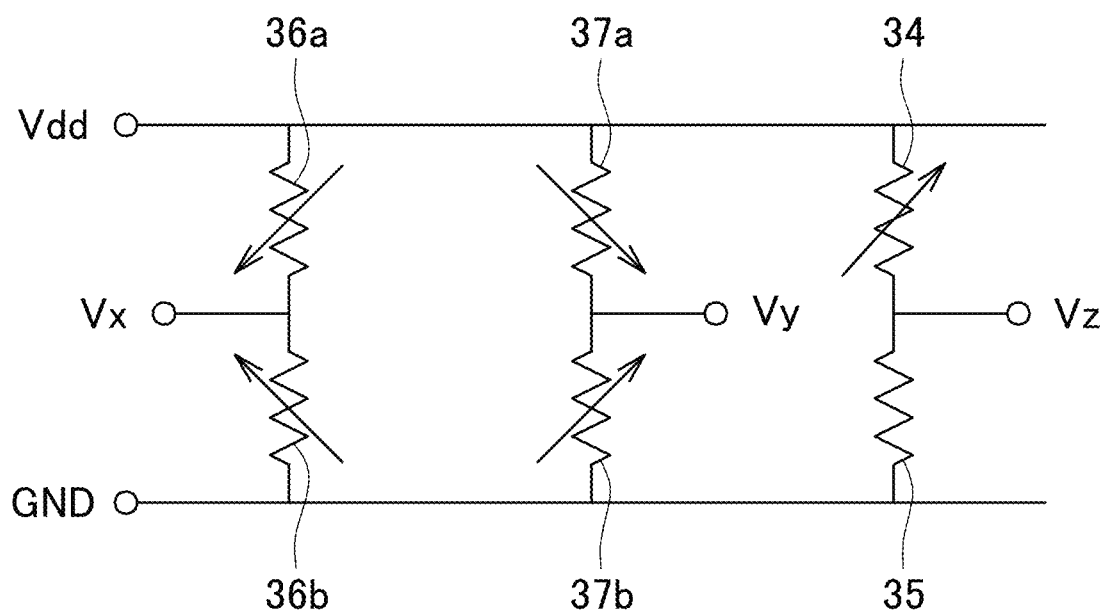
FIG. 7 is a circuit diagram of a strain detection circuit.

The force sensor 30 includes a strain detection circuit detecting the strain of the beam 33. As illustrated in FIG. 7, in the strain detection circuit, the z-axis strain detection element 34 is coupled in series to the reference resistor 35, and a voltage Vdd is applied between both ends of the z-axis strain detection element 34 and the reference resistor 35. Then, the strain detection circuit outputs a voltage Vz between the z-axis strain detection element 34 and the reference resistor 35. The voltage Vz varies in accordance with a change of an electrical resistance of the z-axis strain detection element 34. Thus, by reading the voltage Vz, the strain in the z-axis direction of the beam 33 can be detected. This allows detecting the displacement in the perpendicular direction (the z-axis direction) of the contact element 32. Since an elastic modulus of the beam 33 is already known, from the displacement in the perpendicular direction of the contact element 32, the force in the z-axis direction that the contact element 32 receives from the object, namely, the normal force can be measured.

In the strain detection circuit, the x-axis strain detection element 36a is coupled in series to the x-axis strain detection element 36b, and the voltage Vdd is applied between both ends of the x-axis strain detection element 36a and the x-axis strain detection element 36b. Then, the strain detection circuit outputs a voltage Vx between the x-axis strain detection element 36a and the x-axis strain detection element 36b. The voltage Vx varies by a differential between the x-axis strain detection element 36a and the x-axis strain detection element 36b. Thus, by reading the voltage Vx, the strain in the x-axis direction of the beam 33 can be detected. This allows detecting the inclination in the x-axis direction of the contact element 32. Since the elastic modulus of the beam 33 is already known, from the inclination in the x-axis direction of the contact element 32, the tangential force in the x-axis direction that the contact element 32 receives from the object can be measured.

Similarly, In the strain detection circuit, the y-axis strain detection element 37a is coupled in series to the y-axis strain detection element 37b, and the voltage Vdd is applied between both ends of the y-axis strain detection element 37a and the y-axis strain detection element 37b. Then, the strain detection circuit outputs a voltage Vy between the y-axis strain detection element 37a and the y-axis strain detection element 37b. The voltage Vy varies by a differential between the y-axis strain detection element 37a and the y-axis strain detection element 37b. Thus, by reading the voltage Vy, the strain in the y-axis direction of the beam 33 can be detected. This allows detecting the inclination in the y-axis direction of the contact element 32. Since the elastic modulus of the beam 33 is already known, from the inclination in the y-axis direction of the contact element 32, the tangential force in the y-axis direction that the contact element 32 receives from the object can be measured.

The force sensor 30 can be formed by processing a semiconductor substrate such as an SOI substrate using a semiconductor micro-machining technology. The procedure is, for example, as follows. First, the piezo resistance element and the like are formed on an active layer of the SOI substrate by a method such as impurities diffusion or ion implantation. Subsequently, the strain detection circuit is constituted by forming metal wirings by, for example, aluminum sputtering. Then, a space portion between the frame 31 and the contact element 32 is formed by etching a support substrate by Deep-RIE. The beam 33 is formed by the remaining active layer and an intermediate oxide film.

The manufacturing method of the force sensor 30 is not limited to the semiconductor micro-machining technology. For example, as a material, a metal strain gauge, a stainless steel diaphragm, or the like may be used, or a molding technology by a three-dimensional printer, and the like can be employed.

(Slip Detection)

As described above, the force sensor 30 has a function of measuring the force received from an object. The plurality of force sensors 30 are disposed in the sensor unit 20 in a predetermined distribution. Thus, the sensor unit 20 can measure a distribution of the loads received from the object.

Here, the direction of the force that the force sensor 30 receives from the object is not always perpendicular with respect to the sensing surface. For example, in a case where the grip surface 11s of the grip tool AA is a curved surface, in a case where the surface of the object is a curved surface, in a case where the object has flexibility, in a case where a composition of the object is non-uniform and has different hardness in some positions, and the like, the direction of the force is inclined with respect to the z-axis direction, in some cases. In such cases, magnitude of the force received from the object cannot be accurately obtained only from the normal force (the force in the z-axis direction).

The force sensor 30 of the embodiment can measure the forces in the triaxial directions. Combining the forces in the triaxial directions allows obtaining a combined load. The combined load is obtained by the following Formula 1.

[Formula 1]

$$F=\sqrt{f_x^2+f_y^2+f_z^2} \quad (1)$$

Here, F is the combined load, $f_x$ is the force in the x-axis direction, $f_y$ is the force in the y-axis direction, and $f_z$ is the force in the z-axis direction.

The combined load accurately represents the magnitude of the load received from the object. By using a distribution of the combined load as the load distribution, the slip of the object can be accurately detected. In the following, in the embodiment, the load distribution means a distribution of the combined load.

The load distribution measured by the sensor unit 20 is input in the slip detection device SD. The slip detection device SD detects the slip of the object based on the load distribution. The following describes the procedure.

Slip Detection Method 1

Figure 8C:
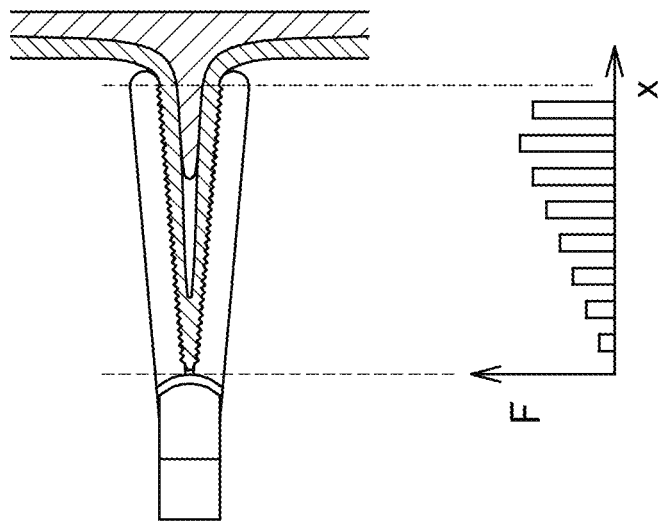
FIG. 8C is a side view and a load distribution in a state where the inner layer is further slipped.
Figure 8B:
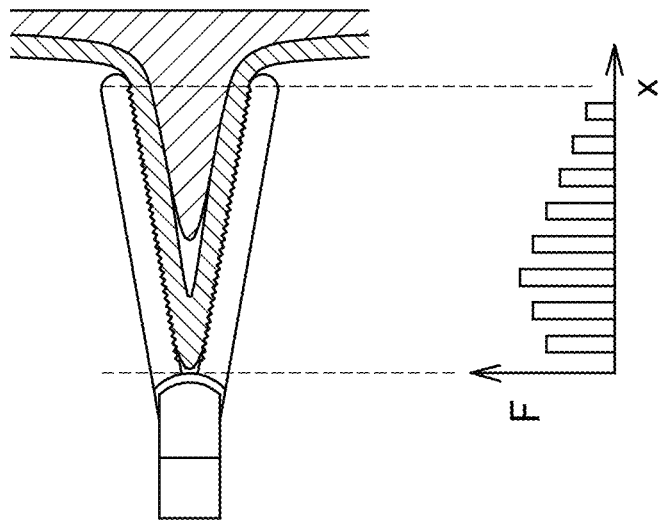
FIG. 8B is a side view and a load distribution in a state where an inner layer is slipped.
Figure 8A:
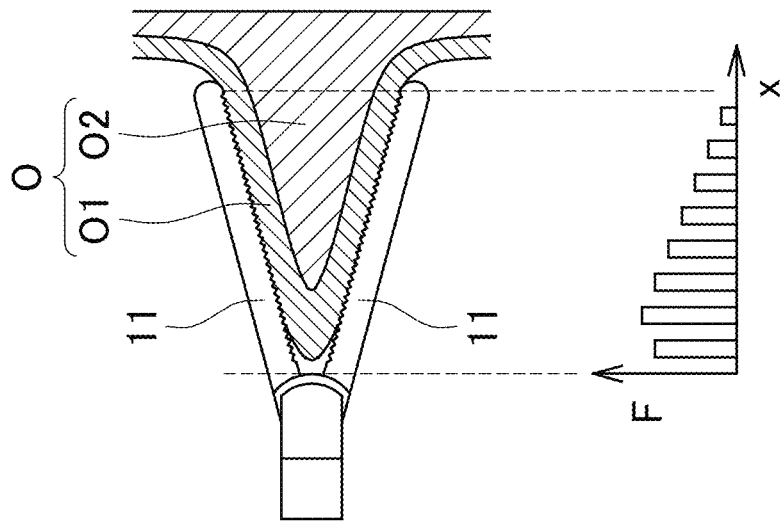
FIG. 8A is a side view and a load distribution in a state where the grip portion firmly grips an object.

As illustrated in FIGS. 8A, 8B, and 8C, it is assumed that the object O has an outer layer O1 and an inner layer O2 like a digestive organ wall. This kind of object O tends to slip between the outer layer O1 and the inner layer O2. FIGS. 8A, 8B, and 8C indicate states where the inner layer O2 slips, in this order. FIGS. 8A, 8B, and 8C also indicate the load distributions measured by the sensor unit 20 in each state.

As illustrated in FIG. 8A, in a state where the grip portions 11, 11 firmly grip the object O, the load distribution that the grip portion 11 receives from the object O has a peak in the vicinity of the base end of the grip portion 11. As illustrated in FIG. 8B, when the inner layer O2 starts to slip with respect to the outer layer O1, the peak of the load distribution moves in the vicinity of a center. Then, As illustrated in FIG. 8C, when the inner layer O2 further slips and moves, the peak of the load distribution moves to the vicinity of the distal end of the grip portion 11. Thus, as the inner layer O2 slips, the peak of the load distribution moves toward the distal end of the grip portion 11 from the base end of the grip portion 11. By using this, the slip of the object O is detected.

A center position of the load distribution is obtained by the following Formula 2, from a balance of a moment.

[Formula 2]
$$x_c = \frac{\sum_{k=1}^{n} x_k F_k}{\sum_{k=1}^{n} F_k} \quad (2)$$

Here, as indicated in FIG. 9, $x_c$ is the center position of the load distribution, $x_k$ is an x-coordinate of a k-th force sensor 30 from the base end of the grip portion 11, $F_k$ is the combined load measured at the k-th force sensor 30.

When the force sensors 30 are disposed at equal intervals at an interval a, the center position $x_c$ of the load distribution can be obtained by Formula 3.

[Formula 3]
$$x_c = \frac{a \sum_{k=1}^{n} (k-1) F_k}{\sum_{k=1}^{n} F_k} \quad (3)$$

The slip detection device SD obtains the center position $x_c$ of the load distribution measured by the sensor unit 20 based on Formula 2 or Formula 3. Then, the slip detection device SD detects the slip of the object based on a temporal change of the center position $x_c$. That is, when the center position $x_c$ is moving, the slip detection device SD determines that the object is slipping. From a movement speed of the center position $x_c$, a speed of the slip of the object can be obtained. Conversely, when the center position $x_c$ is not moving, the slip detection device SD determines that the object is not slipping (firmly gripped).

Slip Detection Method 2

The slip of the object may be detected based on a peak position instead of the center position of the load distribution. Measurement positions of the combined load measured by the sensor unit 20 are discrete. Thus, it is only necessary to specify the peak by fitting the load distribution measured by the sensor unit 20 with a predetermined function. Of the plurality of force sensors 30 that the sensor unit 20 has, a position of the force sensor 30 having the largest combined load measurement value may be set as the peak position.

As described above, the slip detection device SD obtains the peak position of the load distribution measured by the sensor unit 20. Then, the slip detection device SD detects the slip of the object based on a temporal change of the peak position. That is, when the peak position is moving, the slip detection device SD determines that the object is slipping. From the movement speed of the peak position, the speed of the slip of the object can be obtained. Conversely, when the peak position is not moving, the slip detection device SD determines that the object is not slipping (firmly gripped).

In FIGS. 8A, 8B, and 8C, while it is assumed that the object O has the outer layer O1 and the inner layer O2, even for an object having a simple structure that does not have such a structure, the slip can be detected by the above-described methods. An object the surface of which is covered by a lubricant, like melted ice, causes almost no friction with the grip portion 11. For even such an object, the slip can be detected.

As described above, the grip tool AA of the embodiment can measure the load distribution received from the object by the sensor unit 20 disposed in the grip portion 11. Based on the load distribution, the slip of the object can be detected.

In an object where the slip occurs between the outer layer and the inner layer, a frictional force acts between the grip portion 11 and the outer layer, the inner layer slips even when the outer layer does not slip, in some cases. In a slippery object the surface of which is covered with a lubricant, the frictional force generated between the object and the grip portion 11 is very weak. Thus, it is difficult to detect the slip of such an object based on the frictional force.

In contrast to this, in the embodiment, the slip of the object is detected based on the load distribution. Thus, the slip can be detected even in a slippery object that is less likely to cause the frictional force.

(Friction Coefficient Measurement)

Among the forces in the triaxial directions measured by the force sensor 30, the force in the z-axis direction may be regarded as a perpendicular load received from the object, and forces in the x-axis direction and the y-axis direction may be regarded as the frictional force acting with the object. Then, a perpendicular load measurement value and a frictional force measurement value measured by the sensor unit 20 are input into the slip detection device SD. The slip detection device SD obtains the friction coefficient of the object from the perpendicular load measurement value and the frictional force measurement value. The procedure is as follows.

As described above, the slip detection device SD can detect the slip of the object. That is, the slip detection device SD can detect a timing when the object starts to slip. Accordingly, the slip detection device SD can specify a perpendicular load $f_z$ and a frictional force $f_{xy}(0)$ immediately before the object starts to slip. Here, the frictional force $f_{xy}(0)$ is a maximum static frictional force. By using the following Formula 4, the slip detection device SD obtains a static friction coefficient $\mu_0$ between the object and the sensor unit 20 using the perpendicular load $f_z$ and the maximum static frictional force $f_{xy}(0)$.

[Formula 4]
$$\mu_0 = \frac{f_{xy}(0)}{f_z} \quad (4)$$

The slip detection device SD can detect a state where the object is slipping. Accordingly, the slip detection device SD can specify the perpendicular load $f_z$ and a frictional force $f_{xy}$ in the state where the object is slipping. Here, the frictional force $f_{xy}$ is a dynamic frictional force. In accordance with Formula 5 described below, the slip detection device SD obtains a dynamic friction coefficient $\mu$ between the object and the sensor unit 20 from the perpendicular load $f_z$ and the dynamic frictional force $f_{xy}$.

[Formula 5]
$$\mu = \frac{f_{xy}}{f_z} \quad (5)$$

As described above, the slip detection device SD can measure the static friction coefficient and the dynamic friction coefficient of the object. The static friction coefficient and the dynamic friction coefficient represent slipperiness of the object. Accordingly, the slip detection device SD can evaluate the slipperiness of the object.

(Slip Prediction)

The slip detection device SD can also predict a start of slipping of the object. The procedure is as follows.

A preliminarily measured static friction coefficient $\mu_0$ of the object is stored in the slip detection device SD. Based on Formula 4, the slip detection device SD obtains the maximum static frictional force $f_{xy}(0)$ from the static friction coefficient $\mu_0$ and the current perpendicular load measurement value $f_z$.

Then, based on a relation between a current frictional force measurement value $f_{xy}$ and the maximum static frictional force $f_{xy}(0)$, the slip detection device SD predicts the start of slipping. For example, from a differential between the frictional force $f_{xy}$ and the maximum static frictional force $f_{xy}(0)$, an increase rate of the frictional force $f_{xy}$, and the like, the slip detection device SD predicts the start of slipping before the object actually starts to slip.

When a prediction of the start of slipping of the object is reflected to the operation of the grip tool AA, the object can be maintained without slipping. For example, a robot hand or the like is operated by an actuator. When the prediction of the start of slipping of the object is reflected to control on an actuator of this kind of grip tool AA, the object can be maintained without slipping.

In the embodiment, since the plurality of force sensors 30 are disposed side by side in a row, the slip of the object in the row direction (the x-axis direction) can be detected. The direction where the plurality of force sensors 30 are aligned is not limited to the direction (the x-axis direction) toward the distal end of the grip portion 11 from the base end of the grip portion 11. The plurality of force sensors 30 may be aligned in a width direction (the y-axis direction) of the grip portion 11 or may be obliquely aligned inside a x-y plane.

Second Embodiment

Next, a grip system GS according to the second embodiment will be described.

Figure 10:
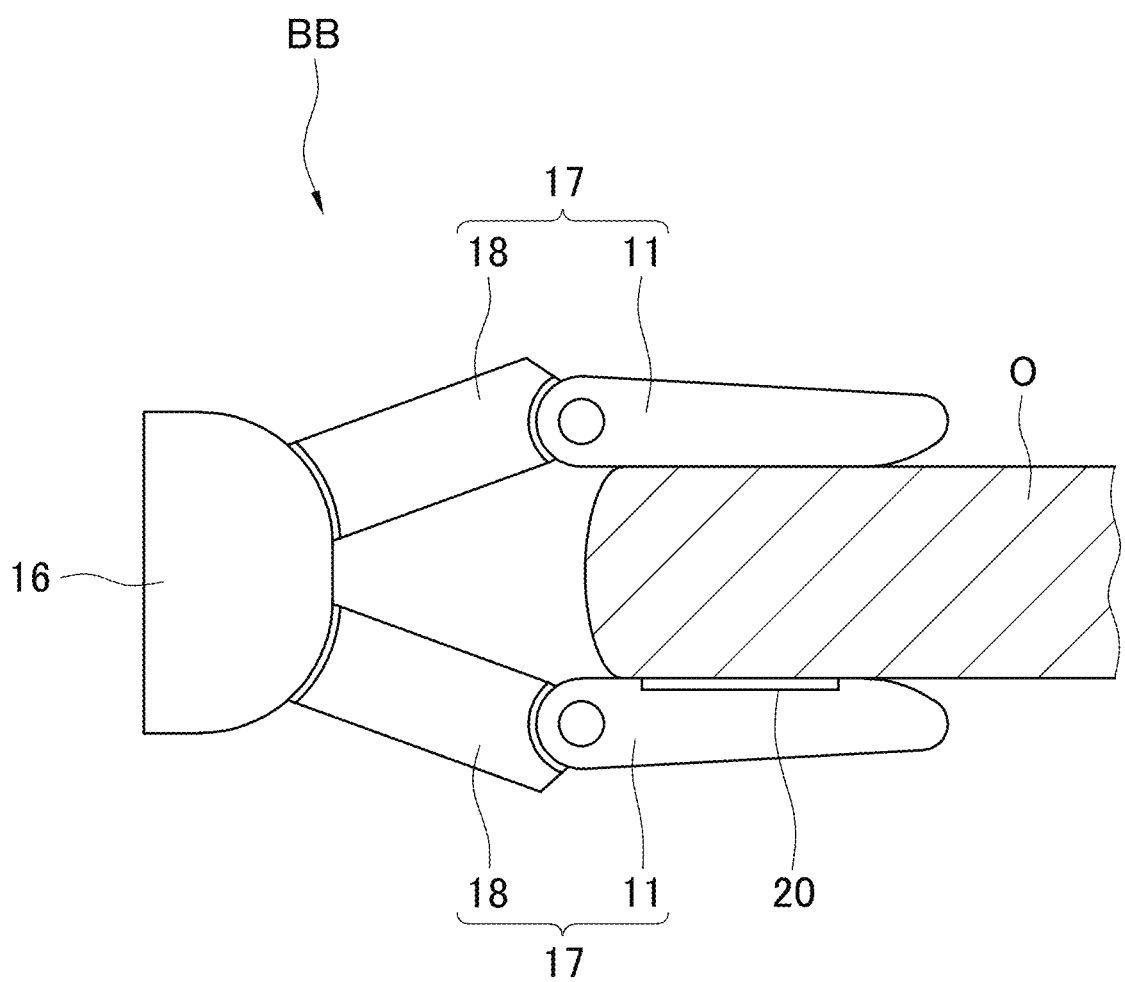
FIG. 10 is a side view of a grip tool of a second embodiment.

As illustrated in FIG. 10, a grip tool BB may be a multi-articulated grip tool. For example, in the grip tool BB, two fingers 17, 17 are disposed in a base portion 16. Each finger 17 is constituted of an intermediate portion 18 and the grip portion 11. The intermediate portion 18 is rotatable with respect to the base portion 16. The grip portion 11 is rotatable with respect to the intermediate portion 18. The object O can be gripped by sandwiching with the fingers 17, 17. One grip portion 11 is disposed with the sensor unit 20.

In a case of such a grip tool BB, the pair of the grip portions 11, 11 open and close while a parallel state is maintained, in some cases. Even in this case, when a margin of the object O is inside the region of the sensor unit 20, similarly to the first embodiment, the slip of the object O can be detected based on the center position or the peak position of the load distribution measured by the sensor unit 20.

As illustrated in FIGS. 11A and 11B, it is assumed that there is a hard portion O3 such as a lump harder than surroundings inside the object O. In this case, in the load distribution measured by the sensor unit 20, the combined load in the region where the hard portion O3 resides becomes higher than other regions. When such object O slips, as the hard portion O3 moves, the region where the combined load is high moves.

For example, as illustrated in FIG. 11A, when the hard portion O3 resides in the vicinity of the base end of the grip portion 11, the load distribution in the region in the vicinity of the base end of the grip portion 11 becomes high. As illustrated in FIG. 11B, when the object O has slipped and the hard portion O3 has moved in the vicinity of the distal end of the grip portion 11, the load distribution in the region in the vicinity of the distal end of the grip portion 11 becomes high. In such a case, similarly to the first embodiment, the slip of the object O can be detected based on the center position or the peak position of the load distribution measured by the sensor unit 20.

As illustrated in FIGS. 12A and 12B, when the object O has a certain degree of hardness, the load distribution measured by the sensor unit 20 reflects a surface shape of the object O. That is, of the surface of the object O, an outwardly protruding portion has the higher combined load, and an inwardly recessed portion has the lower combined load.

Consequently, in a case where the object O slips and moves from the state illustrated in FIG. 12A to the state illustrated in FIG. 12B, the load distribution moves in parallel in a direction where the object O slips while a shape of the load distribution is maintained. In such a case, the slip detection device SD can detect the slip of the object O based on the parallel movement of the load distribution.

Third Embodiment

Next, a grip system GS according to the third embodiment will be described.

As illustrated in FIG. 13, the plurality of force sensors 30 constituting the sensor unit 20 may be disposed so as to be distributed in a plane. The force sensors 30 may be disposed in a square grid shape, in a rectangular grid shape, or in a triangular grid shape.

Thus, when the plurality of force sensors 30 are distributed and disposed in a plane, the slip of an object in a two-dimensional direction can be detected. That is, in addition to the slip in the x-axis direction of the object, the slip in the y-axis direction of the object can be detected.

The plurality of force sensors 30 constituting the sensor unit 20 may be disposed in a cross shape or a T-shape. Even in this way, the slip of the object in the two-dimensional direction can be detected.

Fourth Embodiment

Next, a grip system GS according to the fourth embodiment will be described.

The force sensor 30 may be one that measures only the normal force (the force in the z-axis direction) received from an object. The constitution is not specifically limited, for example, it is only necessary to have a constitution described below.

Figure 14:
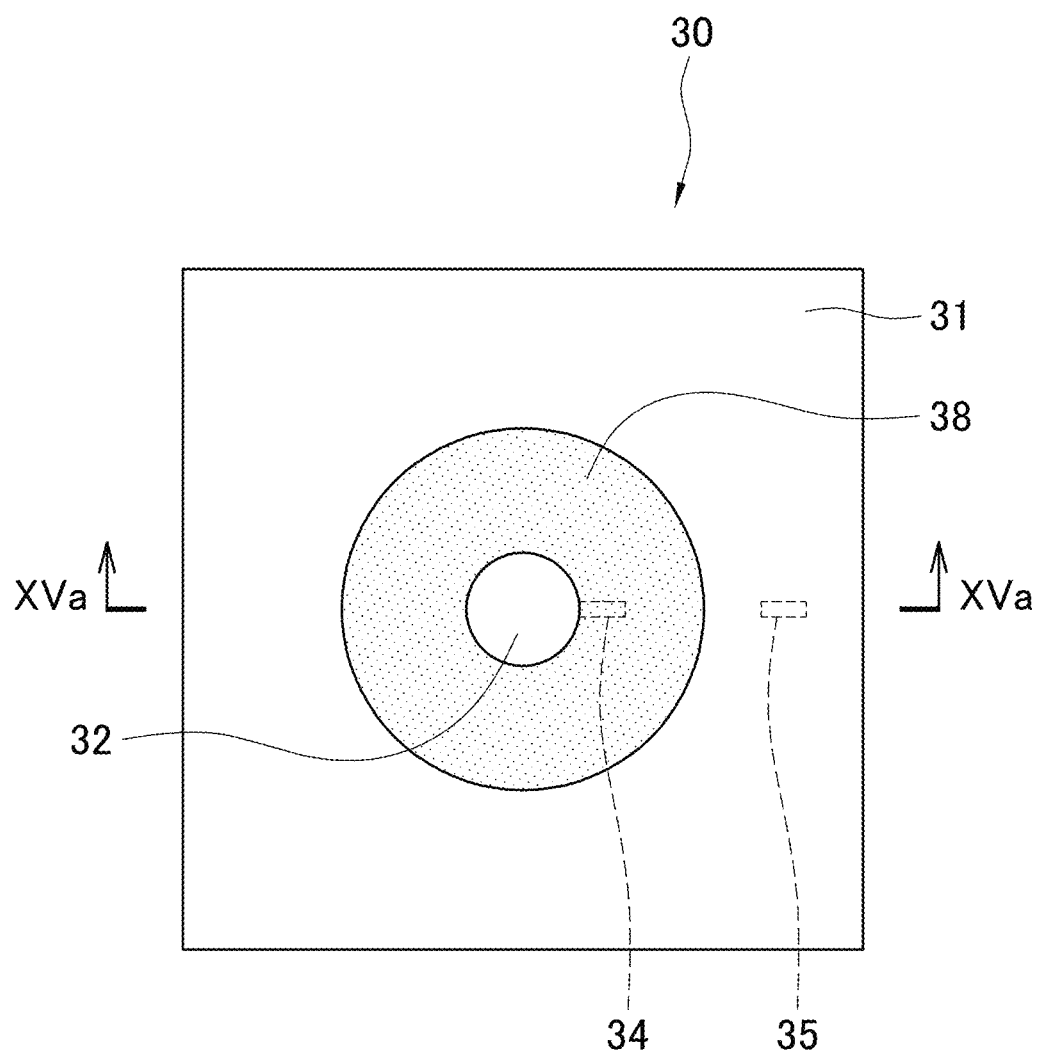
FIG. 14 is a plan view of a force sensor of the third embodiment.

As illustrated in FIG. 14 and FIG. 15A, the force sensor 30 of the embodiment mainly includes the frame 31, the contact element 32, and a diaphragm 38. The frame 31 has a column-shaped space portion. A lower side opening portion of the space portion is closed by the diaphragm 38. The column-shaped contact element 32 is disposed upright in a center of the diaphragm 38. That is, the contact element 32 is disposed in the center of the column-shaped space portion that the frame 31 has. The diaphragm 38 has a thickness of, for example, 10 μm to 30 μm.

As illustrated in FIG. 15B, when the object O comes into contact with the sensing surface of the force sensor 30, the contact element 32 sinks downward (the z-axis direction) due to the load received from the object O. As a result, the diaphragm 38 bends. In order to detect the strain of the diaphragm 38 that occurs at this time, the z-axis strain detection element 34 is disposed in the diaphragm 38. The force sensor 30 is disposed with the reference resistor 35 used in combination with the z-axis strain detection element 34. The reference resistor 35 is disposed at a position that is not affected by the strain of the diaphragm 38, for example, on the lower surface of the frame 31.

Figure 16:
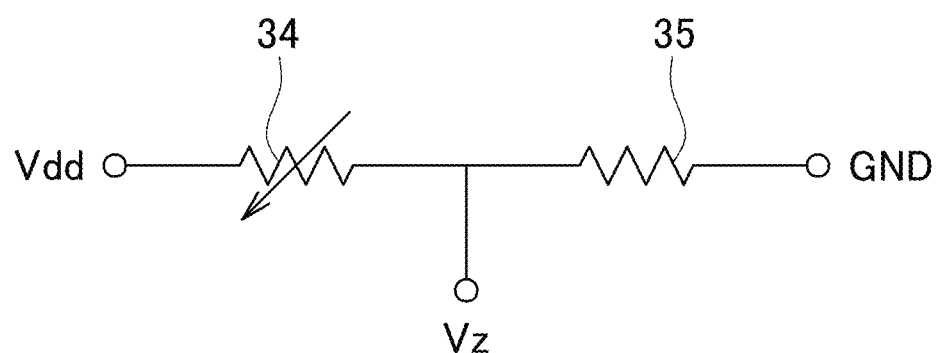
FIG. 16 is a circuit diagram of a strain detection circuit.

The force sensor 30 includes a strain detection circuit that detects the strain of the diaphragm 38. As illustrated in FIG. 16, in the strain detection circuit, the z-axis strain detection element 34 is coupled in series to the reference resistor 35, and the voltage Vdd is applied between both ends of the z-axis strain detection element 34 and the reference resistor 35. Then, the strain detection circuit outputs the voltage Vz between the z-axis strain detection element 34 and the reference resistor 35. The voltage Vz varies in accordance with the change of the electrical resistance of the z-axis strain detection element 34. Thus, by reading the voltage Vz, the strain in the z-axis direction of the diaphragm 38 can be detected. This allows detecting the displacement in the perpendicular direction (the z-axis direction) of the contact element 32. Since an elastic modulus of the diaphragm 38 is already known, from the displacement in the perpendicular direction of the contact element 32, the normal force that the contact element 32 receives from the object can be measured.

Even if the force sensor 30 measures only the normal force, detection of the slip is possible. That is, in the first and second embodiments, it is only necessary to use the perpendicular load (the normal force) instead of the combined load. In this case, the load distribution means the distribution of the perpendicular load.

EXAMPLE

Next, Example will be described.
(Fabrication of Sensor Unit)

The sensor unit was fabricated by processing an n-type SOI wafer including a support substrate thickness of 475 μm and an active layer thickness of 20 μm. With respect to the active layer of the wafer, by performing fabrication processes in the order of formation of a substrate contact region with an $n^+$-type diffusion region, formation of an insulation oxide film, formation of a p-type diffusion layer used for the piezo resistance, and electrode formation with aluminum wirings, a sensing integrated circuit for force detection was formed. The piezo resistance portion was formed by thermal annealing at 1,000° C., after ion implantation at an impurity concentration of $3\times10^{-12}$ $cm^{-2}$. After formation of the circuit portion, a contact element structure formation was performed by Deep-RIE. The contact elements are mechanically supported by the diaphragm structure. The film portion formed by the SOI active layer determines the mechanical properties. Since the piezo resistance is formed on the diaphragm, the signal can be detected by using the displacement of the contact element as a stress change.

FIG. 17 shows a photograph of the completed sensor unit. The sensor unit has a constitution where eight force sensors are aligned in a row. Each force sensor has a size of 1 mm square. The sensor unit was mounted to the grip portion of a forceps.
(Grip of Gel Body)

An object in a gel state was gripped using the forceps where the sensor unit was mounted. FIG. 18A illustrates a state where the gel body is gripped with the entire grip portion of the forceps. This is set as an initial gripping position. FIG. 18B illustrates a state where the gel body is moved by 5 mm from the initial gripping position. FIG. 18C illustrates a state where the gel body is moved by 10 mm from the initial gripping position.

It is seen that as the gel body moves toward the distal end of the grip portion, the peak position of the load distribution also moves toward the distal end of the grip portion. From this, it was confirmed that the slip of the object was able to be detected based on the center position or the peak position of the load distribution.
(Grip of Two-Layer Body)

A two-layer body constituted of an outer layer (a polyethylene film) and an inner layer (a simulated organ) was fabricated by wrapping the simulated organ with the polyethylene film. The fabricated two-layer body was gripped using the forceps where the sensor unit was mounted. FIG. 19A illustrates a state 4.5 seconds after the two-layer body was gripped with the forceps. FIG. 19B illustrates a state 8.2 seconds after the two-layer body was gripped with the forceps. FIG. 19C illustrates a state 16.1 seconds after the two-layer body was gripped with the forceps.

When the two-layer body is gripped with the forceps, the slip occurs between the inner layer and the outer layer, and only the inner layer moves toward the distal end of the grip portion. As a result, the peak position of the load distribution also moves toward the distal end of the grip portion.

Figure 20:
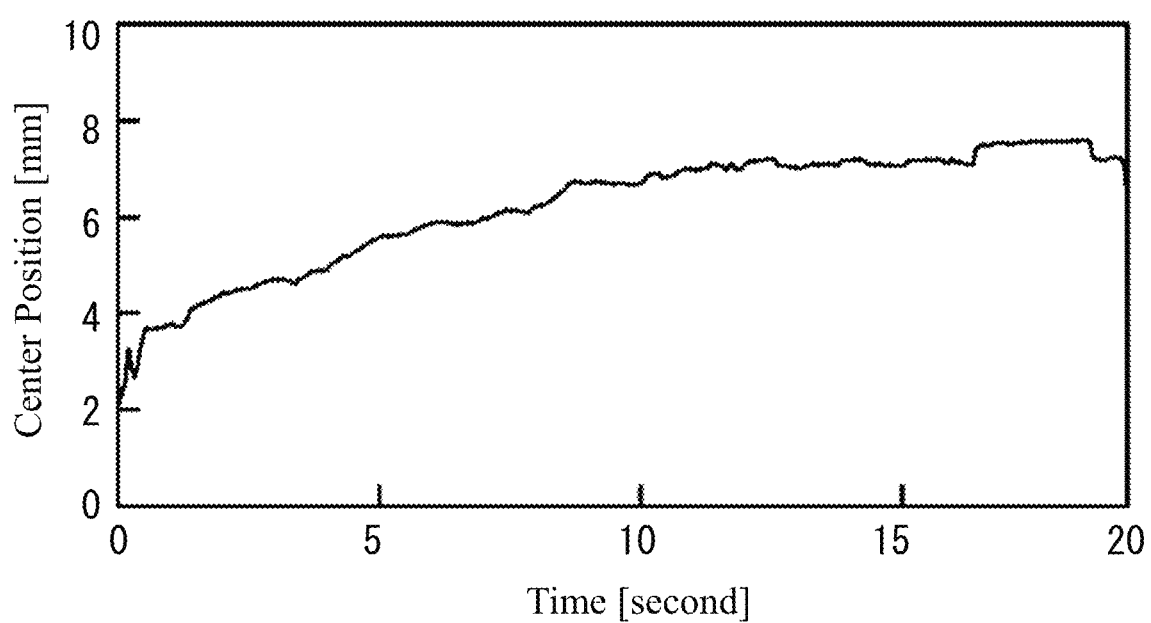
FIG. 20 is a graph illustrating a temporal change of a center position of the load distribution.

FIG. 20 illustrates a temporal change of the center position of the load distribution. The center position of the load distribution moves with passage of time (the slip of the inner layer). From this, it was confirmed that the slip of the object was able to be detected based on the temporal change of the center position of the load distribution.

REFERENCE SIGNS LIST

GS grip system
AA grip tool
11 grip portion
20 sensor unit
30 force sensor
SD slip detection device

The invention claimed is:
1. A grip system comprising:
a grip tool; and
a slip detection device, wherein the grip tool includes:
    a pair of grip portions that sandwiches to grip an object;
    an opening/closing mechanism that opens and closes the pair of grip portions; and
    at least one sensor unit disposed in one or both of the grip portions of the pair of grip portions, wherein
    the at least one sensor unit includes a plurality of force sensors disposed in a predetermined distribution, the plurality of force sensors each have a function of measuring forces in triaxial directions received from the object,
    the slip detection device is configured to detect a slip of the object by using a distribution of a combined load as a load distribution, wherein the combined load is obtained by combining the forces measured in triaxial directions measured by the force sensors, using the following formula

$$F=\sqrt{f_x^2+f_y^2+f_z^2} \qquad (1),$$

where F is the combined load, $f_x$ is the force in an x-axis direction of the triaxial directions, $f_y$ is the force in a y-axis direction of the triaxial directions, and $f_z$ is the force in a Z-axis direction of the triaxial directions.
2. The grip system according to claim 1, wherein the slip detection device is configured to obtain a center position of the load distribution and detect the slip of the object based on a temporal change of the center position.

3. The grip system according to claim 1, wherein the slip detection device is configured to obtain a peak position of the load distribution and detect the slip of the object based on a temporal change of the peak position.

4. The grip system according to claim 1, wherein the slip detection device is configured to detect the slip of the object based on a parallel movement of the load distribution.

5. The grip system according to claim 1, wherein
the slip detection device is configured to obtain a static friction coefficient of the object from a perpendicular load measurement value and a frictional force measurement value measured by the at least one sensor unit immediately before the object starts to slip, and
the slip detection device is configured to obtain a maximum static frictional force from the static friction coefficient and a current perpendicular load measurement value and predict a start of slipping of the object based on a relation between a current frictional force measurement value and the maximum static frictional force.

6. The grip system according to claim 1, wherein a prediction of a start of slipping of the object is reflected to control an actuator of the grip tool.

7. A slip detection device for detecting a slip of an object gripped by a grip tool including a grip portion having a sensor unit with a plurality of force sensors, wherein
the slip detection device is configured to detect the slip of the object by using a distribution of a combined load as a load distribution, the combined load obtained by combining forces in triaxial directions measured by the force sensors, using the following formula $$F=\sqrt{f_x^2+f_y^2+f_z^2} \qquad (1),$$

where F is the combined load, $f_x$ is the force in an x-axis direction of the triaxial directions, $f_y$ is the force in a y-axis direction of the triaxial directions, and $f_z$ is the force in a Z-axis direction of the triaxial directions;
wherein a prediction of a start of slipping of the object is reflected to control an actuator of the grip tool.

8. The slip detection device according to claim 7, wherein the slip detection device is configured to obtain a center position of the load distribution and detect the slip of the object based on a temporal change of the center position.

9. The slip detection device according to claim 7, wherein the slip detection device is configured to obtain a peak position of the load distribution and detect the slip of the object based on a temporal change of the peak position.

10. The slip detection device according to claim 7, wherein the slip detection device is configured to detect the slip of the object based on a parallel movement of the load distribution.

11. The slip detection device according to claim 7, wherein
the slip detection device is configured to obtain a static friction coefficient of the object from a perpendicular load measurement value and a frictional force measurement value measured by the sensor unit immediately before the object starts to slip, and
the slip detection device is configured to obtain a maximum static frictional force from the static friction coefficient and a current perpendicular load measurement value and predict a start of slipping of the object based on a relation between a current frictional force measurement value and the maximum static frictional force.

12. A non-transitory, computer-readable storage medium storing a slip detection program for causing a computer to execute a process for detecting a slip of an object gripped by a grip tool including a grip portion having a sensor unit with a plurality of force sensors, wherein the process includes:
detecting a slip of the object by using a distribution of a combined load as a load distribution, the combined load obtained by combining forces in triaxial directions measured by the force sensors, using the following formula $$F=\sqrt{f_x^2+f_y^2+f_z^2} \qquad (1),$$

where F is the combined load, $f_x$ is the force in an x-axis direction of the triaxial directions, $f_y$ is the force in a y-axis direction of the triaxial directions, and $f_z$ is the force in a Z-axis direction of the triaxial directions;
wherein a prediction of a start of slipping of the object is reflected to control an actuator of the grip tool.

13. The non-transitory, computer-readable storage medium storing the slip detection program according to claim 12, wherein the process includes:
obtaining a center position of the load distribution; and
detecting the slip of the object based on a temporal change of the center position.

14. The non-transitory, computer-readable storage medium storing the slip detection program according to claim 12, wherein the process includes:
obtaining a peak position of the load distribution; and
detecting the slip of the object based on a temporal change of the peak position.

15. The non-transitory, computer-readable storage medium storing the slip detection program according to claim 12, wherein the process includes
detecting the slip of the object based on a parallel movement of the load distribution.

16. The non-transitory, computer-readable storage medium storing the slip detection program according to claim 12, wherein the process further includes:
obtaining a static friction coefficient of the object from a perpendicular load measurement value and a frictional force measurement value measured by the sensor unit immediately before the object starts to slip;
obtaining a maximum static frictional force from the static friction coefficient and a current perpendicular load measurement value; and
predicting a start of slipping of the object based on a relation between a current frictional force measurement value and the maximum static frictional force.

17. A slip detection method for detecting a slip of an object gripped by a grip tool including a grip portion having a sensor unit with a plurality of force sensors, the slip detection method comprising:
detecting a slip of the object by using a distribution of a combined load as a load distribution, the combined load obtained by combining forces in triaxial directions measured by the force sensors, using the following formula $$F=\sqrt{f_x^2+f_y^2+f_z^2} \qquad (1),$$

where F is the combined load, fx is the force in an x-axis direction of the triaxial directions, fy is the force in a y-axis direction of the triaxial directions, and fz is the force in a Z-axis direction of the triaxial directions;
wherein a prediction of a start of slipping of the object is reflected to control an actuator of the grip tool.

18. The slip detection method according to claim 17, wherein the detecting includes:

obtaining a center position of the load distribution; and
detecting the slip of the object based on a temporal change of the center position.

19. The slip detection method according to claim 17, wherein the detecting includes:
obtaining a peak position of the load distribution; and
detecting the slip of the object based on a temporal change of the peak position.

20. The slip detection method according to claim 17, wherein the detecting includes detecting the slip of the object based on a parallel movement of the load distribution.

21. The slip detection method according to claim 17, further comprising:
obtaining a static friction coefficient of the object from a perpendicular load measurement value and a frictional force measurement value measured by the sensor unit immediately before the object starts to slip;
obtaining a maximum static frictional force from the static friction coefficient and a current perpendicular load measurement value; and
predicting a start of slipping of the object based on a relation between a current frictional force measurement value and the maximum static frictional force.

* * * * *